(12) United States Patent
Bannister

(10) Patent No.: US 6,652,875 B1
(45) Date of Patent: Nov. 25, 2003

(54) CASEIN FORMULATIONS FOR THE DELIVERY OF BIOACTIVE CONSTITUENTS

(75) Inventor: Dennis James Bannister, Mount Pleasant (AU)

(73) Assignee: Pacific Biolink Pty. Limited, Hornsby (AU)

( * ) Notice: Subject to any disclaimer, the term of this patent is extended or adjusted under 35 U.S.C. 154(b) by 0 days.

(21) Appl. No.: 09/744,593

(22) PCT Filed: Jul. 29, 1999

(86) PCT No.: PCT/AU99/00608

§ 371 (c)(1),
(2), (4) Date: Mar. 19, 2001

(87) PCT Pub. No.: WO00/06108

PCT Pub. Date: Feb. 10, 2000

(30) Foreign Application Priority Data

Jul. 29, 1998 (AU) .............................................. PP 4947

(51) Int. Cl.$^7$ .......................... A61K 9/68; A61K 33/06; A61K 33/42
(52) U.S. Cl. .......................... 424/440; 424/48; 424/435; 424/682; 424/602; 426/3; 426/74; 426/648; 426/660
(58) Field of Search .......................... 424/49–58, 440, 424/48; 426/72, 74, 645, 3–6, 660

(56) References Cited

U.S. PATENT DOCUMENTS

| | | |
|---|---|---|
| 4,138,477 A | 2/1979 | Gaffar et al. |
| 4,476,142 A | 10/1984 | Netherwood et al. ............ 426/3 |
| 4,582,709 A | 4/1986 | Peters et al. .................... 426/74 |
| 4,911,937 A | 3/1990 | Crosello et al. ............. 426/103 |
| 5,015,628 A | 5/1991 | Reynolds et al. |
| 5,037,639 A | 8/1991 | Tung et al. |
| 5,130,123 A | 7/1992 | Reynolds et al. |
| 5,223,294 A | 6/1993 | Takenawa .................... 426/329 |
| 5,268,167 A | 12/1993 | Tung et al. |
| 5,368,844 A | 11/1994 | Gaffar et al. |
| 5,427,769 A | 6/1995 | Berrocal et al. ............... 424/54 |
| 5,460,803 A | 10/1995 | Tung et al. |
| 5,605,677 A | 2/1997 | Schumann et al. |
| 5,618,517 A | 4/1997 | Miskewitz .................... 424/48 |
| 5,629,035 A | 5/1997 | Miskewitz ..................... 426/5 |
| 5,645,853 A | 7/1997 | Winston et al. .............. 424/440 |
| 5,693,334 A | 12/1997 | Miskewitz .................. 424/440 |
| 5,702,687 A | 12/1997 | Miskewitz .................... 424/52 |
| 5,711,937 A | 1/1998 | Nishida et al. |
| 5,753,296 A | 5/1998 | Girsh ........................ 426/593 |
| 5,766,330 A | 6/1998 | Knights et al. .......... 106/124.2 |
| 5,833,953 A | 11/1998 | Berrocal et al. |
| 5,833,954 A | 11/1998 | Chow et al. |
| 5,879,728 A | 3/1999 | Graff et al. ..................... 426/5 |
| 5,958,380 A | 9/1999 | Winston et al. ............... 424/48 |
| 5,981,475 A | 11/1999 | Reynolds et al |
| 6,103,292 A | 8/2000 | Del Vecchio ............... 426/601 |
| 6,156,367 A | 12/2000 | Keenan et al. .............. 426/565 |
| 6,197,356 B1 | 3/2001 | Girsh ........................ 426/312 |
| 6,365,176 B1 | 4/2002 | Bell et al. .................... 424/439 |
| 6,451,290 B2 | 9/2002 | Winston et al. ............... 424/48 |

FOREIGN PATENT DOCUMENTS

| | | | |
|---|---|---|---|
| AU | 548657 | 8/1981 | |
| AU | 548658 | 8/1981 | |
| AU | 575035 | 5/1984 | |
| AU | 2287283 | 7/1984 | |
| AU | 600225 | 6/1986 | |
| AU | 604046 | 12/1987 | |
| AU | 7737587 | 12/1987 | |
| AU | 601924 | 12/1988 | |
| AU | 629559 | 2/1990 | |
| AU | 622699 | 3/1990 | |
| AU | 626298 | 11/1990 | |
| AU | 602390 | 2/1991 | |
| AU | 653401 | 11/1992 | |
| AU | 658794 | 3/1993 | |
| AU | 670595 | 1/1994 | |
| AU | 718253 | 6/1997 | |
| AU | 746314 | 9/1998 | |
| AU | 732775 | 12/1998 | |
| EP | 0283675 | 9/1988 | |
| FR | 2156149 | 5/1973 | |
| GB | 825115 | 8/1958 | ............... 81/1 |
| JP | 06-179627 | 6/1994 | |
| WO | 8707615 | 12/1987 | |
| WO | 8807862 | 10/1988 | |
| WO | 8909602 | 10/1989 | |
| WO | 9106308 | 5/1991 | |
| WO | 9200756 | 1/1992 | |
| WO | 9200994 | 1/1992 | |
| WO | 9204035 | 3/1992 | |
| WO | WO9303707 | 3/1993 | |
| WO | 9309793 | 5/1993 | |
| WO | 9325583 | 12/1993 | |
| WO | 9400146 | 1/1994 | |
| WO | 9404168 | 3/1994 | |
| WO | 9409799 | 5/1994 | |
| WO | 5228193 | 7/1994 | |

(List continued on next page.)

OTHER PUBLICATIONS

Reeves, et al. "Calcium Phosphate Sequestering Phosphopeptide from Casein." *Science*. vol. 128, p. 472 (1958).

Reynolds, et al. "Cariogenicity of a Confection Supplemented with Sodium Caseinate at a Palatable Level." *Caries. Res.* vol. 23. pp. 368–70 (1989).

Reynolds, et al. "Anticariogenic Complexes of Amorphous Calcium Phosphate Stabilised by Casein Phosphopeptides. A Review." School of Dental Science, The University of Melbourne.

(List continued on next page.)

*Primary Examiner*—Shep K. Rose
(74) *Attorney, Agent, or Firm*—McDonnell Boehnen Hulbert & Berghoff

(57) ABSTRACT

The present invention provides a formulation for the delivery of bioactive constituents to biological surfaces, wherein said formulation comprises a suspensions or solution of at least one isolated and purified casein protein or salt thereof, in water, together with at least one bioactive constituent.

48 Claims, No Drawings

FOREIGN PATENT DOCUMENTS

| WO | 9716542 | 5/1997 |
|---|---|---|
| WO | 1226297 | 7/1997 |
| WO | 9736923 | 10/1997 |
| WO | WO9740811 | 11/1997 |
| WO | 9840406 | 9/1998 |
| WO | 9852524 | 11/1998 |

OTHER PUBLICATIONS

Beddows, C. G. "The Status of Fluoride Added to Bovine Milk." *J. Food Technology.* vol. 17, pp. 55–62 (1982).

Holt, C. "Structure and Stability of Bovine Casein Micelles." *Advances in Protein Chemistry.* vol. 43, pp. 63–151 (1992).

Holt, C. Advanced Dairy Chemistry vol. 3, P. F. Fox, Ed. $2^{nd}$ Ed. Chapman and Hall, London, pp. 233–256 (1997).

Holt, C. Proceedings of $25^{th}$ International Dairy Congress, Sep. 21–24, 1998, *Aarhus, Denmark. II. Dairy Science and Technology*, H. Werner, Ed. Danish National Committee of the IDF, Aarhus, Denmark, pp. 200–208.

Schmidt, D.G. "Properties of Artificial Casein Micelles." *Journal of Dairy Research.* vol. 46, pp. 351–355 (1979).

Schmidt, D.G. "Association of Caseins and Casein Micelle Structure." Developments in Dairy Chemistry–1. Proteins. P.F. Fox, Ed., Applied Science Publishers, London, pp. 61–86 (1982).

Schmidt, D.G. "Properties of Artificial Casein Micelles." *Netherlands Milk and Dairy Journal*, vol. 31, pp. 328–341 (1977).

Schmidt D.G., et al. *Netherlands Milk and Dairy Journal*, vol. 33, pp. 40–48 (1979).

Schmidt, D.G. "Properties of Artificial Casein Micelles," *Netherlands Milk and Dairy Journal.* vol. 33, pp. 40–48 (1979).

McKenzie, H.A. Milk Proteins. Chemistry and Molecular Biology. H.A. MacKenzie, Ed. vol. 2. Academic Press, New York, pp. 3–85 (1971).

Waugh, D.F., et al. "Casein Micelles. Formation and Structure." *Journal of the American Chemical Society.* vol. 87, pp. 2246–2257 (1965).

*Chemical Abstracts*, vol. 126, Abstract No. 73067.

Reynolds, E.C. (1997) Remineralization of enamel subsurface lesions by casein phosphopetpie–stabilised calcium phosphate solutions. *Journal of Dental Research* 76(9): 1587–1595.

Reynolds, E.C. (1995) Anticariogenicity of calcium phosphate complexes of tryptic casein phosphopeptides in the rat. *Journal of Dental Research* 74: 1272–1279.

Sato, R., Noguchi, T. and Naito, H. (1986) Casein phosphopeptide (CPP) enhances calcium absorption from the ligated segment of rat small intestine. J. Nutr. Sci. Vitaminol. 32:67–76.

Gerber, H.W. and Jost R. (1986) Casein phosphopeptides: their effect on calcification of in vitro cultured embryonic rat bone. *Calcif. Tissue Int*. 38:350–357.

Reynolds, E. and Wong, A. (1983) Effect of adsorbed protein on hydroxyapatite zeta potential and Streptococcus mutans adherence. *Infection and Immunity* 39(3): 1285–1290.

Reynolds, E.C. and Del Rio, A. (1984) Effect of casein and whey–protein solutions on caries experience and feeding patterns of the rat. *Arch Oral. Biol.* 29(11): 927–933.

Reynolds, E.C. and Black, C.L. (1987) Reduction of chocolate's cariogenicity by supplementation with sodium caseinate. *Caries Res*. 21: 445–451.

Reynolds, E.C. and Black, C.L. (1987) Confectionary composition and rat caries. *Caries Res*. 21:538–545.

Reynolds, E.C. (1987) The prevention of sub–surface demineralization of bovine enamel and change in plaque composition by casein in an into–oral model. *J. Dental Res*. 66(6): 1120–1127.

Reynolds, E.C., Riley, P.F. and Storey E. (1982) Phosphoprotein inhibition of hydroxapatite dissolution. *Calcif. Tissue Int*. 34: S53–S56.

Miesel, H. and Frister, H. (1988) Chemical characterization of a caseinophophopeptide isolated from in vivo digests of casein diet. *Biol. Chem. Hoppe–Seyler* 369:1275–1279.

Southward, C.R. "Use of caseins and caseinates" in Developments in Dairy Chemistry—4: Functional Milk Proteins, Fox, P.F. (ed), Elsevier, New York, 1989.

Rollema, H.S. "Casein association and micelle formation," in Fox, P.F. (ed) Advanced Dairy Chemistry: Proteins, Kluwer Academic Publishers (1992).

Brignon, G., Ribadeau Duman, B., Mercier, J–C and Pelissier, J–P (1977) Complete amino acid sequence of bovine βs2–casein. FEBS Letters 76(2): 274–279.

Morr, C.V. (1979) "Conformation and functionality of milk proteins", in Functionality and protein structure, Gould, R.F. ed. ACS Symposium series, Washington DC.

Dagleish, G. and Law, A.J.R. (1988) Sodium caseinates—composition and properties of different preparations. *Journal of the Society of Dairy Technology* 41(1): 1–4.

Lieska, B. and Konrad, G. (1994) Thermal modification of sodium–caseinate. 1. Influence of temperature and pH on selected physico–chemical and functional properties. *Milchwissenschaft* 49(1): 16–20.

Mohanty, B., Mulvihill, M. and Fox P.F. (1988) Emulsifying and foaming properties of acidic caseins and sodium caseinate. *Food Chemistry* 28: 17–30.

Schmidt, K., and McNeil, V. (1993) Effect of heat treatments on the functional properties of caseinate and whey protein isolate solutions, *Milchwissenschaft* 48(1): 3–5.

Food Chemicals Codex, Food and Nutrition Board, Division of Biological Sciences, Assembly of Life Sciences, National Reseach Council, National Academy Press, Washington DC, 1981.

Food Additives, Branen, A., Davidson, P. and Salminen, S eds, Marcel Dekker, New York, 1990.

# CASEIN FORMULATIONS FOR THE DELIVERY OF BIOACTIVE CONSTITUENTS

TECHNICAL FIELD

The invention relates to formulations designed to deliver bioactive constituents to biological surfaces, in particular, but not limited to, dental surfaces.

BACKGROUND ART

The casein formulations of the prior art have not described an isolated and purified casein protein, together with at least one bioactive constituent, wherein the formulation provides a delivery system for the bioactive constituent, whilst at the same time maintaining the activity of the casein protein and associated bioactive constituent. Further, the formulations of the prior art suffer from a number of significant disadvantages. For example, the prior art formulations have a limited shelf life at room temperature, before the occurrence of odorous bacterial breakdown or the appearance of a precipitate of protein resulting from the addition of incompatible components.

The present invention provides a formulation for the delivery of bioactive constituents to biological surfaces, wherein said formulation comprises at least one isolated and purified casein protein or salt thereof, together with at least one bioactive constituent. Further, such a formulation displays an extended shelf life, whilst maintaining the activity of the casein protein and associated bioactive constituent, and a formulation which with added dispersing agents provides an increased dissolution rate for pre-dried formulations in aqueous solutions.

OBJECT OF THE INVENTION

An object of the invention is to provide a casein protein based formulation which acts as a delivery system for bioactive substances.

DISCLOSURE OF THE INVENTION

According to a first embodiment of the invention, there is provided a formulation for the delivery of bioactive constituents to biological surfaces, wherein said formulation comprises a suspension or solution of at least one isolated and purified casein protein or salt thereof, in water, together with at least one bioactive constituent.

Typically, the formulation delivers the bioactive constituents to biological surfaces in mammals. More typically, the biological surfaces include dental surfaces, such as teeth and gums. Even more typically, the biological surfaces include all tissues of the oral cavity, but can also include skin, and the alimentary tract, including the linings of the stomach and intestinal walls.

Typically, the biological activity of the casein protein within the formulation is maintained regardless of the bioactive constituent associated therewith.

Typically, the casein protein present in the formulation may be present as a mixture of any two or more of the casein proteins outlined below.

Typically, the isolated and purified casein protein may comprise a casein protein as disclosed in Whitney, R. Proteins of Milk. In: Fundamentals of diary chemistry 3rd Edn. (1988) (ed. N. P. Wong), Van Nostrand Reinhold, N.Y. USA, pages; 82–91, the disclosure of which is incorporated herein by reference. More typically, the casein protein is selected from the group consisting of: α-casein, β-casein, κ-casein, and mixtures thereof. Yet even more typically, the casein protein is selected from the group consisting of:

A. $\alpha_{S1}$-Caseins
  1. $\alpha_{S1}$-Casein $X^n$—8P (genetic variants—A, B, C, D-9P, and E)
  2. $\alpha_{S1}$-Casein $X^a$—9P (genetic variants—A, B, C, D-10P, and E)
  3. $\alpha_{S1}$-Casein fragments B. $\alpha_{S1}$-Caseins
  1. $\alpha_{S1}$-Casein $X^a$—10P (genetic variants—A, B, C-9P, and D-7P)
  2. $\alpha_{S1}$-casein $X^a$—11P (genetic variants—A, B, C,-10, and D-8P)
  3. $\alpha_{S1}$-Casein $X^a$—12P (genetic variants—A, B, C-11P, and D-9P)
  4. $\alpha_{S1}$-Casein $X^a$—13P (genetic variants—A, B, C-12P, and D-10P)

C. β-Caseins
  1. β-Casein $X^a$—5P (genetic variants—$A^1$, $A^2$, $A^3$B, C-4P, D-4P, and E)
  2. β-Casein $X^a$—1P (f29–209) (genetic variants—$A^1$, $A^2$, $A^3$, and B)
  3. β-Casein $X^a$—(f106–209) (genetic variants—$A^2$, $A^3$, and B)
  4. β-Casein $X^a$—(f108–209) (genetic variants—A and B)
  5. β-Casein $X^a$—4P (f1–28)$^b$
  6. β-Casein $X^a$—5P (f1–105)$^b$
  7. β-Casein $X^a$—5P (f1~107)$^b$
  8. β-Casein $X^a$—1P (f29~105)$^b$
  9. β-Casein $X^a$—1P (f29~107)$^b$ D. κ-Caseins
  1. κ-Casein $X^a$—1P (genetic variants—A and B)
  2. Minor κ-caseins $X^a$—1, —2, —3, etc. (genetic variants—A and B)

Generally, the casein protein is a phosphoprotein, and may be present in the form of a salt. Typically, the salts are selected from the group consisting of: alkaline metals or alkaline earth metals. More typically, the alkaline earth metals are selected from the group consisting of: sodium, calcium, zinc, copper, aluminium, potassium, strontium, magnesium and nickel salts.

Typically, the casein phosphoprotein is in the form of a divalent or trivalent metal ion complex or aggregate. More typically, the casein phosphoprotein is in the form of caseinate calcium phosphate or caseinate calcium fluorophosphate. Even more typically, the casein phosphoprotein is in the form of casein calcium phosphate complex or caseinate calcium fluorophosphate complex.

Typically, the formulation of the present invention also includes a phosphatase inhibitor. More typically, the phosphatase inhibitor is selected from the group consisting of: fluoride ions, vinyl ether maleic acid polymers, and divalent and trivalent metal ions.

Typically, the casein protein may be isolated and purified from bovine, ovine or caprine milk. More typically, the casein protein for use in the invention is any commercially available casein protein.

Note that unless otherwise stated, all percentages of components of the formulation are by weight, based on the total weight of the formulation.

Typically, the amount of casein protein, typically, present as casein phosphoprotein, in the formulation is between about 0.05 and about 50%. More typically, the amount of casein phosphoprotein present in the formulation is between about 0.5 and about 25%. Even more typically, the amount of casein phosphoprotein present in the formulation is between about 1 and about 20%. Still more typically, the amount of casein phosphoprotein present in the formulation is between about 1 and about 15%. Yet still more typically, the amount of casein phosphoprotein present in the formulation is between about 1 and about 10%.

Typically, the isolated and purified casein protein, and at least one bioactive constituent are present in association within the formulation in accordance with the present invention. More typically, the association between the isolated and purified casein protein and the bioactive constituent is by virtue of the presence of both negative and positive groups associated along the length of the casein polypeptide chain, wherein these groups can ionically interact with a range of bioactive constituents to form a complex with the isolated and purified casein protein to be soluble in water. Even more typically, wherein the bioactive constituents include constituents insoluble in water, the constituents may be stabilised in an emulsion or suspension within the casein protein formulation of the present invention. Thus, the formulation of the present invention comprising a suspension or solution of at least one isolated and purified casein protein, together with at least one bioactive constituent, provides a delivery system for a range of bioactive constituents.

In particular, casein protein, typically, casein phosphoprotein has an affinity for biological surfaces, and as a consequence, when the formulation in accordance with the present invention is applied to a biological surface, by virtue of this affinity of the casein protein resident in the formulation, the concentration of the associated bioactive constituent at the biological surface is increased, thereby providing a delivery system wherein the bioactive constituent is presented to the biological surface.

Typically, inorganic bioactive constituents are selected from the group consisting of: calcium, phosphate, fluorophosphate, fluoride, zirconia, magnesium, barium, zinc, iron, copper, aluminium, tin, silver, and salts of said bioactive constituents, selected from the group consisting of: titanium dioxide, zinc oxide, calcium fluoride, sodium fluoride, stannous fluoride, calcium phosphate, calcium fluorophosphate and calcium oxide. In a typical form of the invention, the casein phosphoprotein acts to sequester the bioactive constituents, calcium and phosphate to form an amorphous complex, which can then be used as a soluble source of calcium and phosphate ions.

Typically, fluoride sources used in the formulation of the present invention include: sodium fluoride, stannous fluoride, sodium monofluorophosphate, zinc ammonium fluoride, tin ammonium fluoride, calcium fluoride or cobalt ammonium fluoride.

Fluoride ions are typically provided at a level of from about 0 ppm to 6000 ppm, more typically 0 to 3000 ppm, even more typically, 5 to 1500 ppm and still more typically, 50 to 1500 ppm.

For example, the inorganic bioactive constituents, or for that matter, organic bioactive constituents, may function to safeguard the formulation against ultra-violet or visual light radiolytic degradation, which for example, may occur during the use of the formulation in the filling of a dental cavity.

Typically, surfactants, such as soap, anionic, nonionic, cationic, amphoteric and/or zwitterionic surfactants, may also be present in the formulation as a bioactive constituent, or as an additional agent within the formulation. More typically, the surfactants are present within the range of 0 to 15%, even more typically 0.1 to 15%, still more typically 0.25 to 10% by weight. Anionic surfactants are most preferred, such as sodium dodecyl sulfate, sodium lauryl sarcosinate and sodium dodecylbenzone sulphonate.

Typically, the amount of inorganic bioactive constituents present in the formulation is between about 0.0005 and about 50%. More typically, the amount of inorganic constituents present in the formulation is between about 0.2 and about 35%. Even more typically, the amount of bioactive inorganic constituents present in the formulation is between about 0.5 and about 15%. Yet even more typically, the amount of inorganic bioactive constituents present in the formulation is between about 0.5 and about 10%.

Typically, bioactive constituents may comprise organic bioactive constituents which bind to the casein protein, yet do not affect its biological activity. More typically, the organic bioactive constituents are selected from the group consisting of: octymethoxycinnamate, butyl methoxydibenzoylmethane, or other commercially available ultra-violet or visual light absorbing compounds. More typically, organic bioactive constituents include the antimicrobial agents outlined below.

In addition, in terms of the formulation in accordance with the first embodiment of the invention, the organic bioactive constituents may also include corticosteroid hormones, such as cortisol, adrenocorticotropin, corticotropin; pain killing agents such as aspirin and/or paracetamol; vitamins and/or optical brighteners for improvement in the appearance of teeth, such as stilbene disulphonic acid. Many of the organic bioactive constituents safeguard the formulation against ultra-violet or visual light radiolytic degradation, or may even be applied to the skin for the prevention of sunburn.

Typically, the amount of organic constituents present in the formulation is between about 0.005 and about 30%. More typically, the amount of organic constituents present in the formulation is between about 1 and about 20%. Even more typically, the amount of organic constituents present in the formulation is between about 1 and about 15%. Still more typically, the amount of organic constituents present in the formulation is between about 1 and about 5%.

Typically, the formulation as defined in accordance with the first embodiment of the invention is capable of accepting a suitable amount of a thickening agent to form a thixotropic gel, wherein the biological activity of the casein protein within said thixotropic gel is maintained.

Typically, the thickening agent is selected on the basis that it does not deactivate the active casein protein component of the formulation. For instance, the thickening agents of the present invention do not cause flocculation or precipitation of the protein within the formulation. More typically, the thickening agent is selected from the group consisting of: a synthetic or natural clay, a synthetic or natural polymer, or a combination of any of these. Even more typically, the thickening agent includes a clay chosen from the group consisting of laponite (any form of laponite, such as laponite DF), hectorite, calcium montmorillonite, sodium montmorillonite (bentonite), sodium exchange montmorillonite, acid activated bleaching earth and palygorskite. Still more typically, the laponite includes any form of available laponite.

The thickening agent may be selected from the natural polymers: alginate, cellulose and cellulose derivatives. The thickening agent may be selected from the synthetic polymer: carboxymethyl cellulose.

Other suitable thickening agents include Irish moss, gum tragacanth, starch polyvinylpyrrolidone, hydroxyehtylpropylcellulose, hydroxybutyl methyl cellulose, hydroxypropyl methyl cellulose, hydroxyethyl cellulose (e.g. available as Natrosol), sodium carboxymethyl cellulose, and colloidal silica such as finely ground Syloid.

Typically, the amount of thickening agent present in the formulation is between 0 and about 20%. More typically, the amount of thickening agent present in the formulation is between 0 and about 15%. Even more typically, the amount of thickening agent present in the formulation is between 0 and about 6%.

Typically, particulate inorganic bioactive constituents may be added to the formulations of the present invention in the form of thixotropic gels, wherein the insoluble bioactive constituent(s) are held in suspension by the thixotropic gel, and not necessarily through interaction with the resident casein protein. More typically, these inorganic bioactive constituents are selected from the group consisting of titanium dioxide, zinc oxide, zirconia, calcium fluoride, stannous fluoride and calcium oxide. Still more typically, the presence of particulate inorganic bioactive constituents also improve the visibility of the thixotropic gel formulation, and thus its ease of application to a biological surface, such as teeth.

The isolated and purified casein protein present in the formulation as defined in accordance with the first embodiment of the invention may also be subjected to bacterial contamination and odorous breakdown. Therefore, the bioactive constituent present in the formulation may itself be at least one antimicrobial agent, or may further comprise at least one antimicrobial agent as a further bioactive constituent, together with other bioactive constituents. Typically, any antimicrobial agent used in commerce is also suitable for use in the formulation of the present invention. More typically, the antimicrobial agent may include an organic antimicrobial agent, wherein the organic antimicrobial agent is typically water-soluble. Even more typically, the antimicrobial agent comprises organic antimicrobial agents as disclosed in U.S. Pat. No. 5,368,844, the disclosure of which is incorporated herein by reference.

As described in U.S. Pat. 5,368,844 the antimicrobial agent comprises: halogenated diphenyl ethers, such as: 2,4,4-trichloro-2-hydroxy-diphenyl ether (Triclosan); phenolic compounds, including phenol and its homologues, such as: 2-methyl-phenol, 3-methyl-phenol, 4-methyl-phenol, 4-ethyl-phenol, 2,4-dimethyl-phenol, 3,4-dimethyl-phenol, 2,6-dimethyl-phenol, 2,2-methylene bis (4-chloro-6-bromo-phenol); mono- and poly-alkyl and aromatic halophenols, including -p-chlorophenols such as: methyl-p-chlorophenol, ethyl-p-chlorophenol, n-propyl-p-chlorophenol, n-butyl-chlorophenol: -o-chlorophenols; p-bromophenols; -O-bromophenols; resorcinol and its derivatives, such as: n-methyl hexyl resorcinol; bisphenolic compounds and halogenated carbanilides.

Still more typically, the antimicrobial agent may be selected from the group consisting of: glycerol, ethanol, sorbitol, mannitol, sodium benzoate, methyl-p-hydroxybenzoate, ethyl-p-hydroxybenzoate, N-propyl p-hydroxybenzoate, butyl-p-hydroxybenzoate, phenoxy ethanol and quaternary ammonium salts, such as benzethonium chloride, and diisobutyl-phenoxyethoxyethyl dimethyl benzyl ammonium chloride.

Other types of antimicrobial agents may includes amidines, such as substituted guanidine, including, chlorhexidine, and other known bis-biguanidines; and cationic tertiary amines.

Typically, where the antimicrobial agent is sodium benzoate, the amount of sodium benzoate present in the formulation is between about 0.0001 and about 0.5%. More typically, the amount of sodium benzoate present in the formulation is between about 0.005 and about 0.3%. Even more typically, the amount of sodium benzoate present in the formulation is between about 0.0025 and about 0.2%. Yet even more typically, the amount of sodium benzoate present in the formulation is between about 0.001 and about 0.1%.

Typically, the amount of ethanol present in the formulation is between about 0.05 and about 20%. More typically, the amount of ethanol present in the formulation is between about 0.5 and about 10%. Even more typically, the amount of ethanol present in the formulation is between about 1 and about 8%. Yet even more typically, the amount of ethanol present in the formulation is between about 2 and about 6%.

Typically, the formulations of the present invention can be incorporated into vehicles such as: chewing gums, lozenges, foods, confectionary, pharmaceutical compositions, toothpaste creams or gels, or mouthwashes.

A series of further ingredients may typically be included in toothpaste and gels in accordance with the invention, and they include: abrasive polishing materials, sudsing agents, flavouring agents, humectants, binders, sweetening agents, and water.

Typically, abrasives used in the formulations of the invention, may include alumina and hydrates thereof, such as amorphous silica, alpha alumina trihydrate, magnesium trisilicate, dicalcium phosphate, magnesium carbonate, aluminosilicate, such as calcined aluminium silicate and aluminium silicate, calcium carbonate, zirconium silicate, polymethylmethacrylate, powdered polyethylene, polypropylene, silica xerogels, hydrogels and aerogels and the like. Also suitable as abrasive agents are calcium pryophosphate, insoluble sodium metaphosphate, calcium carbonate, dicalcium orthophosphate, particulate hydroxyapatite and the like. Depending on the form which the oral formulation is to take, the abrasive may be present in an amount of from 0 to about 70% by weight, typically about 1 to about 70% by weight, more typically from about 10 to about 70% by weight, particularly for toothpastes.

Humectants contemplated for use in the formulations of the present invention include: glycerol, polyol, sorbitol, polyethylene glycols, propylene glycol, hydrogenated partially hydrolysed polysaccharides and the like. The humectants are generally present in amounts of from 0 to about 80%, typically about 5 to about 70% by weight, particularly for toothpastes.

Various other materials may be incorporated in the oral formulations of the present invention, such as whitening agents, preservatives, silicones, chlorophyll compounds, other anticalculus agents, and/or ammoniated material such as urea, diammonium phosphate, and mixtures thereof. These adjuvants, where present are incorporated in the preparations in amounts which do not substantially aversely affect the properties and characteristics desired.

Any suitable flavoring or sweetening material may also be employed. Examples of suitable flavouring constituents are flavouring oils. For example, oil of spearmint, peppermint, wintergreen, sassafras, clove, sage, eucalyptus, marjoram, cinnamon, lemon, and orange, and methyl salicylate. Suitable sweetening agents include sucrose, lactose, maltose, dextrose, levulose, sorbitol, xylitol, d-tryptophan, dihydrochalcones, sodium cyclamate, perillartine, APM (aspartyl phenyl alanine, methyl ester), and saccharine. Suitably, flavouring and sweetening agents may together comprise from about 0.1% to about 10% by weight or more of the preparation, and more typically, from about 0.1% to about 5% by weight or more of the preparation.

As described above, the formulations of the present invention may be present in the form selected from the group consisting of: a toothpaste, mouthwash, food-stuff, beverage, a pharmaceutical composition, dentifrice, or a confectionary. More typically, the food-stuff may include breakfast foods, such as cereals, and the confectionary may include chewing gum, candies, sweets, chocolates and other confectionary-like products.

Formulations of the present invention can be incorporated in lozenges, or in chewing gum or other similar products, for example, by stirring an aqueous suspension or solution and/or combination thereof, of the formulation, or a pre-dried form of the formulation in solid or redissolved form into a warm gum base topical vehicle or coating the outer surface of a gum base. Typical of these include jelutone, rubber latex, vinylite resins, and desirably with conventional plasticisers or softeners, sugar or other sweeteners or carbohydrates such as glucose, sorbitol and the like.

More typically, formulations in accordance with the first embodiment of the invention may be dried, for example, by spray drying, and then added to substances, such as lozenges, chewing gums, carbonated beverages, sat, sugar, artificial sweeteners, baked goods, toothpaste, mouthwash, and other oral hygiene products.

A preferred form of the present invention is a chewing gum including the formulation in accordance with the first embodiment of the invention. The chewing gum may be made from any gum base composition well known in the art and includes those gum bases utilised for conventional chewing gums and bubblegums. Gum bases typically include a polymeric material and may comprise elastomers, resins, polyvinyl acetates, waxes, facts, oils, emulsifiers, fillers and antioxidants.

Typically, a chewing gum in accordance with the present invention may comprise ingredients present in amounts selected from the following ranges: typically, between about 10 to about 80%, more typically, between about 25 to about 80%, even more typically, between about 40 to about 80%, of a gum base; typically, about 0.1 to about 40%, more typically, about 0.1 to about 25%, even typically, about 1 to about 10% of a pre-dried form of the formulation in accordance with the first embodiment of the invention; typically, between about 5 to about 70%, more typically, between about 10 to about 50%, even more typically, between about 25 to about 40% of a water-soluble bulking ingredient; typically, between 0 to about 5% of a flavourant, more typically, between 0 to abut 3.5% of a flavourant; even more typically, between 0 to about 2% of a flavourant; typically, between 0 to about 0.2%, more typically, between 0 to about 0.1%, even more typically between 0 to about 0.05% of a colourant; typically, between 0 to about 20%, more typically, between 0 to abut 15%, even more typically, between 0 to about 10% of an abrasive; typically, between 0 to about 3%, more typically, between 0 to about 2%, even more typically, between 0 to about 1% of a surfactant; and typically, between 0 to about 3%, more typically, between 0 to about 2% even more typically, between 0 to about 1% of a fluoridating agent.

As outlined above, unless otherwise stated all percentages of components of the chewing gum form of the formulation are by weight, based on the total weight of the chewing gum composition.

Typically, the chewing gum may be any variety of different chewing gum types including low and high moisture, sugar or sugarless, wax-containing or wax-free, low calorie, and the like, and can contain other bioactive agents, other than casein protein.

In general, a chewing gum product generally consists of a water-insoluble gum base, a water-soluble portion, and flavours. The water-soluble portion dissipates over a period of time, and the gum base portion is retained during mastication. Further, a conventional chewing gum base usually contains an elastomer, an elastomer solvent, and various other ingredients such as fillers, softeners, plasticizers and emulsifiers.

Typically, chewing gum base elastomers include: chicle, jetutong, balata, crown gum, guttapercha, sorva, lechi capsi, sorva, crown gum, nispero, rosidinha, perillo, niger gutra, tunu, gutta kay, pendare, leche de vaca, chiquibul, crown gum, and the like, butadiene-styrene copolymer, polyisobutylene, isobutylene-isoprene copolymer, polyethylene, and the like, and mixtures thereof. More typically, the amount of elastomers employed in the gum base composition varies greatly depending upon factors such as the type of gum base used, the consistency of the gum base composition desired, and the other components used in the composition to make the final chewing gum product. Even more typically, the elastomer is present in the gum base composition in an amount of between any one of the following: about 15% to about 60%; about 15% to about 30%; or about 25% to about 30%.

Typically, elastomer solvents are also present in the gum base composition, wherein they act in softening or plasticising the elastomer component. Chewing gum base elastomer solvents include pentaerythritol ester of wood rosin, glycerol ester of polymerised rosin, partially hydrogenated methyl ester of rosin, and the like. More typically, the elastomer solvent may be employed in the gum base composition in an amount of from about 2% to about 40%, and even more typically, from about 7% to about 15%.

Typically, waxes, fats/oils are also present in the gum base composition, wherein they act to improve the elasticity of the gum base. Waxes can provide a soft or firm chew, influence the flavour release and provide bulkiness and smoothness to the gum base. The fats, oils and waves may be used individually or in combination in the gum base, and may be of mineral, animal, vegetable or synthetic origin. Examples of waxes include paraffin, microcrystalline waxes, polyethylene wax, paraffin wax, beeswax, carnauba wax, microcrystalline wax, carnauba wax, candellila wax, rice bran wax, esparto wax, flax wax, sugarcane wax, and synthetic waxes.

Further, examples of suitable oils and fats useable in gum compositions include hydrogenated or partially hydrogenated vegetable or animal fats, and these may be selected from the group consisting of: cottonseed oil, soybean oil, coconut oil, palm kernel oil, beef tallow, hydrogenated tallow, lard, cocoa butter, lanolin and the like; fatty acids such as palmitic, oleic, stearic, linoleic, lauric, myristic, caproic, caprylic, decanoic or esters and salts as sodium stearate and potassium stearate. More typically, these ingredients when used are generally present in amounts up to about 8%, and even more typically up to about 4%.

Generally, the gum base composition may also include effective amounts of fillers or bulking agents, which act to increase firmness and bulk and influence the texture and the flavour release of the chewing gum. Typically, fillers may include organic compounds (mineral adjuvants) such as calcium carbonate, magnesium carbonate, ground limestone, magnesium silicate, calcium phosphate, cellulose polymers, clay, alumina, aluminium hydroxide, aluminium silicate, talc, tricalcium phosphate, dicalcium phosphate, and mixtures thereof.

More typically, the amount of the filler present in the gum base composition in an amount from about 1% to about 40%, still more typically, from about 5% to about 20%.

Chewing gum compositions generally include sugar and sugar alcohol sweeteners, having a range in sweetening intensity, which may also act as bulking agents. For example, in sugarless gum compositions, a sweetening agent, such as sorbital or other sugar alcohol, may act as a bulking agent.

Typically, sugar based sweetening/bulking agents include: monosaccharides, disaccharides and polysaccharides. More typically, the polysaccharides may be selected from the group consisting of: xylose, ribulose, glucose (dextrose), mannose, galactose, fructose (levulose), sucrose, maltose, and mixtures thereof. Further, typical sugar alcohol bulking agents include sorbitol, xylitol, mannitol, galactitol, maltitol, mixture of alpha-D-glucopyranosyl-1 6-mannitol and alpha-D-glucopyranosyl-1 6-sorbitol, maltodextrins, hydrogenated starch hydrolysates; hydrogenated hexoses; hydrogenated disaccharides; and the like, and mixtures thereof. Even more typically, the bulking agents/sweeteners may be present in an amount from about 15% to about 90%, and still more typically, in an amount from about 25% to about 65%, and even more typically, from about 30% to about 50%.

More typically, the chewing gum compositions may also include a high intensity sweetening agent. More typically, the agent is selected from the group consisting of: dihydrochalcone, monellin, steviosides, glycyrrhizin, dihydroflavenol, and L-aminodicarboxylic acid, aminoalkenoic acid ester amides, saccharin and salts thereof, 3,4-dihydro-6-methyl-1,2,3-oxathiazine-4-one-2,2-dioxide and salts thereof, and L-aspartic acid derived sweeteners, such as Aspartame, Alitame, and derivatives of chlorodeoxysucrose or chlorodeoxygalactosucrose.

Typically, the amount of sweetener employed in the chewing gum composition will vary with the sweetener selected for a particular chewing gum and the level of sweetness desired. More typically, the sweeteners are usually present in an amount from about 1% to about 70% and still more typically, in an amount from about 40% to about 50%. Still more typically, the intense sweeteners are usually used in an amount of up to about 1%, and even more typically, from about 0.05% to about 0.4%.

Typically, chewing gum composition may also contain a flavoring agent, and more typically, the flavouring agent is in an amount from about 0.02% to about 5%.

Typically, chewing gum composition may also comprise additives selected from the group consisting of: colouring agents such as: titanium dioxide, incorporated in amounts up to about 2%; thickening agents such as: methyl cellulose, alginates, carrageenan, xanthan gum, gelatin, carob, tragacanth, and locust bean, and fillers.

Typically, in the lozenge according to the present invention, the topical vehicle or carrier in a tablet or lozenge is a solid water-soluble polyhydric alcohol (polyol) such as mannitol, xylitol, sorbitol, malitol, a hydrogenated starch hydrolysate. Lycasin, hydrogenated glucose, hydrogenated disaccharides, and hydrogenated polysaccharides in an amount of about 90 to 98% by weight of the total composition. Solid salts such as sodium bicarbonate, sodium chloride, potassium bicarbonate or potassium chloride may totally or partially replace the polyol carrier.

Typically, the formulation of the present invention can be applied topically to biological surfaces within the oral cavity, such as teeth and/or gums, as described in accordance with any one of the second to twenty-sixth embodiments of the invention as outlined below. More typically, in regard to the application of the formulation of the present invention to teeth, this may involve application of the formulation to a cavity, followed by cavity closure through application of a dental cavity filling composition, or dental capping.

Typically, when applying the formulation within the oral cavity, advantage is taken of the ability of casein protein to adhere to dental surfaces, thereby ensuring both the casein protein, and the bioactive constituent(s) present in the formulation are provided at close proximity to the dental surface, wherein the bioactive constituents include those outlined above.

Typically, the formulation in accordance with the first embodiment of the invention may also be present in the form of a mouthwash. More typically, in this form the bioactive constituent present in the mouthwash may be a suitable amount of an antimicrobial agent. Even more typically, the antimicrobial agent includes those antimicrobial agents defined above.

Typically mouthwashes comprise a water/alcohol solution, flavour, humectant, sweetener, sudsing agent, and colorant. The corresponding compounds mentioned above in relation to toothpastes and other oral formulations, are generally suitable and useful within the ranges for mouthwashes as well. For example, the mouthwash can typically include ethanol at a level of from 0 to about 60%, more typically from about 5 to about 30% by weight.

According to a second embodiment of the invention, there is provided a method of treating or preventing dental caries and/or tooth erosion in humans or animals in need of said treatment and/or prevention, wherein said method comprises administering a therapeutically effective amount of the formulation in accordance with the first embodiment of the invention, wherein said formulation is capable of controlling or preventing dental caries and/or tooth erosion in humans or animals.

According to a third embodiment of the invention, there is provided the formulation in accordance with the first embodiment of the invention, when used in the treatment and/or prevention of dental caries and/or tooth erosion in humans or animals in need of said treatment and/or prevention.

According to a fourth embodiment of the invention, there is provided use of the formulation in accordance with the first embodiment of the invention, in the preparation of a medicament for he treatment and/or prevention of dental caries and/or tooth erosion in humans or animals in need of said treatment and/or prevention.

Typically, treatment or prevention of dental caries and/or tooth erosion involves release of bioactive constituents from the formulation. More typically, the bioactive constituents of the formulation as described in relation to the treatment and/or prevention of dental caries and/or tooth erosion, include: polyphosphates, generally employed in the form of their wholly or partially dehydrated polyphosphate water-soluble alkali metal, or ammonium salt, such as, tetrasodium pyrophosphate; N-methylpyrrolidone or pyrrolidone-5,5-diphophosphonic acids, such as, 2-pyrrolidone-5,5-diethyl phosphoric acid.

Typically, the amount of bioactive constituents of the formulation as described in relation to the treatment and/or prevention of dental caries and/or tooth erosion, is between about 0.01 to about 40% of the formulation. More typically, between about 0.01 to about 25% of the formulation. Still more typically, between about 0.1 and about 15% of the formulation. Yet still more typically, between about 0.1 and about 10% of the formulation.

According to a fifth embodiment of the invention, there is provided a method of treating and/or preventing dental sensitivity in humans or animals in need of said treatment and/or prevention, said method includes administering an effective amount of the formulation in accordance with the first embodiment of the invention, wherein said formulation is capable of controlling or preventing dental sensitivity in humans or animals.

According to a sixth embodiment of the invention, there is provided the formulation in accordance with the first embodiment of the invention, when used in the treatment and/or prevention of dental sensitivity in humans or animals in need of said treatment and/or prevention.

According to a seventh embodiment of the invention, there is provided use of the formulation in accordance with the first embodiment of the invention, in the preparation of a medicament for the treatment and/or prevention of dental sensitivity in humans or animals in need of said treatment and/or prevention.

More typically, the bioactive constituents of the formulation as described in relation to the treatment and/or prevention of dental sensitivity in accordance with the fifth, sixth or seventh embodiments of the invention include: glycerinc, strontium chloride, sodium citrate, potassium nitrate or dicalcium phosphate.

Typically, the amount of bioactive constituents of the formulation as described in relation to the treatment and/or prevention of dental sensitivity in accordance with the fifth, sixth or seventh embodiments of the invention is between about 0.001 to about 60% of the formulation. More typically, between about 0.01 to about 50% of the formulation. Still more typically, between about 0.1 to about 35% of the formulation. Yet still more typically, between about 0.1 to about 20% of the formulation.

According to an eighth embodiment of the invention, there is provided a method of treating or preventing gingivitis in humans or animals in need of said treatment and/or prevention, said method includes administering an effective amount of the formulation in accordance with the first embodiment of the invention, wherein said formulation is capable of controlling or preventing gingivitis in humans or animals.

According to a ninth embodiment of the invention, there is provided the formulation in accordance with the first embodiment of the invention, when used in the treatment and/or prevention of gingivitis in humans or animals in need of said treatment and/or prevention.

According to a tenth embodiment of the invention, there is provided use of the formulation in accordance with the first embodiment of the invention, in the preparation of a medicament for treatment and/or prevention of gingivitis in humans or animals in need of said treatment and/or prevention.

According to an eleventh embodiment of the invention, there is provided a method of treating or preventing mouth odour in humans or animals, said method includes administering an effective amount of the formulation in accordance with the first embodiment of the invention, wherein said formulation is capable of controlling or preventing mouth odour in humans or animals in need of said treatment and/or prevention.

According to a twelfth embodiment of the invention, there is provided the formulation in accordance with the first embodiment of the invention, when used in controlling or preventing mouth odour in humans or animals in need of said treatment and/or prevention.

According to a thirteenth embodiment of the invention, there is provided use of the formulation in accordance with the first embodiment of the invention, in the preparation of a medicament for controlling or preventing mouth odour in humans or animals in need of said treatment and/or prevention in need of said treatment and/or prevention.

Typically, treatment and/or prevention of gingivitis and/or mouth odour involves release of bioactive constituents from the formulation. More typically, the bioactive constituents of the formulation as described in relation to the treatment and/or prevention of the relevant disorder in accordance with any one of the eighth to thirteenth embodiments of the invention include an antimicrobial agent.

Typically, the antimicrobial agent includes those antimicrobial agents described above in relation to the first embodiment of the invention. More typically, the antimicrobial agent may include an organic antimicrobial agent, wherein the organic antimicrobial agent is typically water-soluble. Even more typically, the antimicrobial agent may include organic antimicrobial agents as disclosed in U.S. Pat. No. 5,368,844, the disclosure of which is incorporated herein by reference. Still more typically the antimicrobial agent may be selected from the group consisting of: ethanol, sorbitol, mannitol, sodium benzoate, methyl-p-hydroxybenzoate ethyl-p-hydroxybenzoate, N-propyl p-hydroxybenzoate, butyl-p-hydroxybenzoate, phenoxy ethanol and quaternary ammonium salts.

Typically, the amount of sodium benzoate present in the formulation is between about 0.0001 and about 0.5%. More typically, the amount of sodium benzoate present in the formulation is between about 0.005 and about 0.3%. Even more typically, the amount of sodium benzoate present in the formulation is between about 0.0025 and about 0.2%. Yet even more typically, the amount of sodium benzoate present in the formulation is between about 0.001 and about 0.1%.

Typically, the amount of ethanol present in the formulation is between about 0.05 and about 20%. More typically, the amount of ethanol present in the formulation is between about 0.5 and about 10%. Even more typically, the amount of ethanol present in the formulation is between about 1 and about 8%. Yet even more typically, the amount of ethanol present in the formulation is between about 2 and about 6%.

According to a fourteenth embodiment of the invention, there is provided a method of recrystallising and/or remineralising enamel and/or dentine in humans or animals in need of said recrystallising and/or remineralising, said method includes administering an effective amount of the formulation in accordance with the first embodiment of the invention, wherein said formulation is capable of recrystallising and remineralising enamel and/or dentine in humans or animals.

According to a fifteenth embodiment of the invention, there is provided the formulation in accordance with the first embodiment of the invention, when used in recrystallising and/or remineralising enamel and/or dentine in humans or animals in need of said recrystallising and/or remineralising.

According to an sixteenth embodiment of the invention, there is provided use of the formulation in accordance with the first embodiment of the invention, in the preparation of a medicament for recrystallising and/or remineralising enamel and/or dentine in humans or animals in need of said recrystallising and/or remineralising.

Typically, recrystallising and remineralising enamel and/or dentine involves release of bioactive constituents from the formulation. More typically, the bioactive constituents of the casein protein formulation include; fluoride, a calcium phosphate complex or a calcium fluorophosphate complex, wherein said calcium phosphate/fluorophosphate complex provides a soluble (bioavailable) source of calcium and/or phosphate.

Typically, the amount of fluoride present in the formulation is in the range of about 1 ppm to about 6000 ppm. More typically, the amount of fluoride present in the formulation is in the range of about 5 ppm to about 250 ppm. Even more typically, the amount of fluoride present in the formulation is in the range of about 25 ppm to about 100 ppm.

Typically, the amount of soluble calcium or phosphate so provided is in the range of about 0.01 mg/mL to about 25 mg/mL. More typically, the amount of soluble calcium or phosphate is in the range of about 0.1 mg/mL to about 20 mg/mL. Even more typically, the amount of soluble calcium or phosphate so provided is in the range of about 0.1 mg/mL to about 10 mg/mL.

According to a seventeenth embodiment of the invention, there is provided a method of buffering plaque against a decrease in pH in humans or animals in need of said buffering, said method includes administering an effective amount of the formulation in accordance with the first embodiment of the invention, wherein said formulation is capable of buffering plaque against a fall in pH in humans or animals.

According to an eighteenth embodiment of the invention, there is provided the formulation in accordance with the first embodiment of the invention, when used in buffering plaque against a decrease in pH in humans or animals in need of said buffering.

According to a nineteenth embodiment of the invention, there is provided use of the formulation in accordance with the first embodiment of the invention, in the preparation of a medicament for buffering plaque against a decrease in pH in humans or animals in need of said buffering.

Typically, the casein protein within the formulation will alone provide a buffering action in relation to the plaque. More typically, the buffering action in relation to the plaque involves release of bioactive constituents from the casein protein formulation, such as orthophosphate. Typically, the amount of orthophosphate provided is in the range of about 0.1 mg/mL to about 50 mg/mL; more typically, in the range of about 0.5 mg/mL to about 25 mg/mL; still more typically, in the range of about 5 mg/mL to about 10 mg/mL.

According to a twentieth embodiment of the invention, there is provided a method of treating and/or preventing osteoporosis in humans or animals in need of said treatment and/or prevention, said method includes administering an effective amount of the formulation in accordance with the first embodiment of the invention, wherein said formulation is capable of controlling or preventing osteoporosis in humans or animals.

According to a twenty-first embodiment of the invention, there is provided the formulation in accordance with the first embodiment of the invention, when used in treating and/or preventing osteoporosis in humans or animals in need of said treatment and/or prevention.

According to a twenty-second embodiment of the invention, there is provided use of the formulation in accordance with the first embodiment of the invention, in the preparation of a medicament for treating and/or preventing osteoporosis in humans or animals in need of said treatment and/or prevention.

More typically, the treatment and/or prevention of osteoporosis, the bioactive constituents of the formulation include: vitamin D, or a calcium phosphate complex and/or calcium fluorophosphate complex, wherein said calcium phosphate complex and/or calcium fluorophosphate complex provides a soluble (bioavailable) source of calcium.

Typically, the amount of soluble calcium provided is in the range of about 0.1 mg/mL to about 20 mg/mL; more typically, in the range of about 0.5 mg/mL to about 15 mg/mL; still more typically, in the range of about 0.5 mg/mL to about 10 mg/mL.

Typically, the amount of vitamin D provided is in the range of about 0.1 mg/mL to about 100 mg/mL; more typically, in the range of about 0.1 mg/mL to about 75 mg/mL; still more typically, in the range of about 0.1 mg/mL to about 50 mg/mL; even more typically, in the range of about 1 mg/mL to about 25 mg/mL.

As described in relation to the treatment and/or prevention of the relevant disorder in accordance with any one of the twentieth to twenty-second embodiments of the invention, in the formulation of the invention, the bioactive constitute comprises vitamin D, or a calcium phosphate complex and/or calcium fluorophosphate complex, is usually used continuously over a period of 3 to 36 months. Dosages of the formulation anti-atypical mycobacterial agents are generally in accordance with known dosage ranges for the treatment and/or prevention of osteoporosis. For example, the typical dosage of the formulation is from 250 mg to 1.5 g per day, more typically about 750 mg per day; even more typically about 450 mg per day. Alternatively, the dosage regimen may be expressed as typically, from about 1 mg/kg to about 15 mg/kg per day, more typically about 2 mg/kg to 8 mg/kg per day; even more typically about 500 mg per day.

The treatment of osteoporosis may be monitored by standard procedures in the art, including various blood parameters, during the course of treatment in accordance with the invention.

According to a twenty-third embodiment of the invention, there is provided a method of treating and/or preventing calculus formation in the oral cavity of humans or animals in need of said treatment and/or prevention, said method includes administering an effective amount of the formulation in accordance with the first embodiment of the invention, wherein said formulation is capable of controlling or preventing calculus formation in the oral cavity of humans or animals in need of said treatment and/or prevention.

According to a twenty-fourth embodiment of the invention, there is provided the formulation in accordance with the first embodiment of the invention, when used in treating and/or preventing calculus formation in the oral cavity in humans or animals in need of said treatment and/or prevention.

According to a twenty-fifth embodiment of the invention, there is provided use of the formulation in accordance with the first embodiment of the invention, in the preparation of a medicament for treating and/or preventing calculus formation in the oral cavity in humans or animals in need of said treatment and/or prevention.

Typically, in the treatment and/or prevention of calculus formation in accordance with any one of the twenty-third to twenty-fifth embodiments of the invention, the bioactive constituents of the formulation may include the casein protein, present in the form of a phosphoprotein. Even more typically, the bioactive constituents of the formulation include polyphosphates, such as tetrasodium pyrophosphate, tetrapotassium pyrophosphate, and mixtures thereof.

Typically, the amount of phosphoprotein present in the formulation described in relation to the treatment and/or prevention of calculus formation is between about 0.05 to about 50% of the casein protein formulation. More typically, the amount of phosphoprotein present in the formulation is between about 0.5 and about 25%. Even more typically, the amount of phosphoprotein present in the formulation is between about 1 and about 20%.

Typically, the amount of polyphosphate present in accordance with any one of the twenty-third to twenty-fifth embodiments of the invention is between about 0.05 to about 25% of the casein protein formulation. More typically, the amount of polyphosphate present in the formulation is between about 0.5 and about 15%. Even more typically, the amount of polyphosphate present in the formulation is between about 1 and about 10%.

Typically as described in relation to the treatment and/or prevention of the relevant disorder in accordance with any one of the second to twenty-fifth embodiments of the invention, the treatment and/or prevention of the relevant disorder may be achieved via an oral formulation according to the first embodiment of the invention, present in a form such as a dentifrice, and preferably applied by brushing regularly within the oral cavity, thereby applying the formulation to the teeth and gums. Typically, the regularity of brushing may range from every second or third day, to preferably from 1 to 3 times daily, and may take place over a duration of at least 2 weeks up to 8 weeks or more, and even up to lifetime. Still more typically, the treatment and/or prevention of the relevant disorder takes place at a pH of about 4.5 to 10, generally about 5.5 to 9, and more preferably about 6 to 8. The dentifrice is typically removed by rinsing with water after each application.

Alternatively, as described in relation to the treatment and/or prevention of the relevant disorder in accordance with any one of the second to twenty-fifth embodiments of the invention, the treatment and/or prevention of the relevant disorder may be achieved via an oral formulation according to the first embodiment of the invention, present in a form such as a mouthwash, and preferably applied by rinsing regularly within the oral cavity, thereby applying the formulation to the teeth and gums. Typically, the regularly of rinsing may range from every second or third day, to preferably from 1 to 3 times daily, and may take place over a duration of at least 2 weeks up to 8 weeks or more, and even up to lifetime. Still more typically, the treatment and/or prevention of the relevant disorder takes place at a pH of about 4.5 to 10, generally about 5.5 to 9, and more preferably about 6 to 8.

Alternatively, as described in relation to the treatment and/or prevention of the relevant disorder in accordance with any one of the second to twenty-fifth embodiments of the invention, the treatment and/or prevention of the relevant disorder may be achieved via an oral formulation according to the first embodiment of the invention, present in a form such as a thixotropic gel, and preferably applied by applying the gel regularly within the oral cavity, thereby applying the formulation to the teeth and gums. Typically, the regularity of gel application may range from every second or third day, to preferably from 1 to 3 times daily, and may take place over a duration of at least 2 weeks up to 8 weeks or more, and even up to lifetime. Still more typically, the treatment and/or prevention of the relevant disorder takes place at a pH of about 4.5 to 10, generally about 5.5 to 9, and more preferably about 6 to 8. The dentifrice is typically removed by rinsing with water after each application.

More typically, as described in relation to the treatment and/or prevention of the relevant disorder in accordance with any one of the second to twenty-fifth embodiments of the invention, the formulations so described may be present in the form selected from the group consisting of: a toothpaste, mouthwash, food-stuff, beverage, pharmaceutical composition, dentifrice, or a confectionary. More typically, the food-stuff may include breakfast foods, such as cereals, and the confectionary may include chewing gum, candies, sweets, chocolates and other confectionary-like products.

Typically, formulations of the present invention, for use in any one of the second to twenty-fifth embodiments of the invention, can be incorporated in lozenges, or in chewing gum or other products, for example, by stirring an aqueous suspension or solution and/or combination thereof, of the formulation, or a pre-dried form of the formulation in solid or redissolved form, into a warm gum base topical vehicle or coating the outer surface of a gum base. Typical of these include jelutone, rubber latex, vinylite resins, and desirably with conventional plasticisers or softeners, sugar or other sweeteners or carbohydrates such as glucose, sorbitol and the like.

More typically, formulations in accordance with the first embodiment of the invention, for use in any one of the of the second to twenty-fifth embodiments of the invention, may be dried, for example, by spray drying, and then added to substances, such as lozenges, chewing gums, carbonated beverages, salt, sugar, artificial sweeteners, baked goods, toothpaste, mouthwash, and other oral hygiene products.

According to a twenty-sixth embodiment of the invention, there is provided a glass ionomer cement, wherein said cement comprises the formulation in accordance with the first embodiment of the invention, together with liquid and powdered precursors of said glass ionomer cement capable of reacting to form said glass ionomer cement.

Typically, the glass ionomer cement is obtainable by curing a composition comprising a mixture of a liquid precursor of a glass ionomer cement, comprising polymerisable monomers, a carboxylic acid polymer, a solvent, a free radical initiator and an activator for the free radical initiator; and a powdered precursor of a glass ionomer cement, wherein said liquid precursor of a glass ionomer cement, said powdered precursor of a glass ionomer cement are in a ratio typically from between about 2.5:1 to about 1:1 by weight, and wherein said curing is achieved by a free radical polymerisation reaction.

The polymerisable acid or non-acidic monomer may be present in an amount up to 90% by weight based on the total of the liquid precursor of the glass ionomer cement. Typically, the polymerisable acid or non-acidic monomer is present in a range of between about 2 to about 50% by weight, more typically in a range between about 2 to about 45%, about 2 to about 40%, about 2 to about 35%, about 5 to abut 35%, about 8 to about 35%, about 10 to about 35% to about 35%, or about 12 to about 33% by weight, and even more typically in a range between about 15 to about 35% by weight.

Typically, the carboxylic acid polymer may be present in an amount up to about 90% by weight based on the total of the liquid precursor of the glass ionomer cement. Typically, the carboxylic acid polymer is present in a range of between about 5 to about 50% by weight, more typically in a range between about 5 to about 45%, about 5 to about 30%, about 5 to about 25%, about 10 to about 45%, or about 10 to about 40% by weight, even more typically in a range between about 15 to about 40% by weight.

Similarly, the aqueous solvent may be present in an amount up to about 80% by weight based on the total of the liquid precursor of the glass ionomer cement. Typically, the aqueous solvent is present in a range of between about 10 to about 75% by weight, and more typically in a range between about 30 to about 50% by weight.

Where the material is obtained through a free radical polymerisation curing process, a free radical initiator may be present in an amount up to about 5% by weight based on the total of the liquid precursor of the glass ionomer cement. Typically, the free radical initiator is present in a range of between about 0.01 to about 2% by weight, and more typically in a range between about 0.1 to about 0.5% by weight.

An activator for the free radical initiator may be present in an amount up to about 5% by weight, based on the total of the liquid precursor of the glass ionomer cement. Typically, the activator is present in a range of between about 0.01 to about 2% by weight, and more typically in a range between about 0.1 to about 0.5% by weight.

The liquid precursor of the glass ionomer cement may be comprised of a variety of polymerisable acid or non-acidic monomers, including any acidic or non-acidic monomers that will take part in a free radical polymerisation reaction. Acid monomers are those acids that contain carbon-carbon double bonds. These include methacrylic acid, acrylic acid, itaconic acid, maleic acid, and maleic anhydride. The polymerisable non-acidic monomers may include such monomers as: 2-hydroxy ethyl methacrylate, acrylamide, methacrylamide, or tetrahydrofurfuryl methacrylate. Further, these polymerisable monomers may also be combined with acidic or neutral monomers containing more than one carbon-carbon double bond such as: 1,5-diallyl-2,4-benzene dicarboxylic acid, triethylene glycol dimethacrylate or triallyl-1,3,5-triazine-2,4,6(1H,3H,5H)-trione.

The liquid precursor of the glass ionomer cement may be comprised of a variety of carboxylic acid polymers including any homopolymers with a single type of unit along their side chain, such as poly(acrylic acid) poly(methacrylic acid), and (itaconic acid). The carboxylic acid polymers may also include any copolymers, such as poly(vinyl methyl ether co-maleic acid), poly(methacrylic acid co-acrylic acid), poly (styrene co-acrylic acid co-methacrylic acid). Furthermore, the polymer may have double bonds along the side chain, making the polymer capable of taking part in a free radical reaction.

The liquid precursor of the glass ionomer cement will contain an amount of an aqueous solvent. Suitable aqueous solvents include water, but may also include a mixture such as water and a water miscible liquid such as ethanol or isopropanol.

Both the liquid and powdered precursors of the glass ionomer cement may also contain a free radical initiator such as camphorquinone, azobisisobutyronitrile or riboflavin.

The liquid precursor of the glass ionomer cement may also contain a free radical inhibitor such as butylated hydroxytoluene, hydroquinone and methyl ethyl hydroquione.

Suitable powdered precursors of the glass ionomer cement include any powder containing any amount of divalent or trivalent metal ions. Examples of these include calcium aluminum fluorosilicate glass, phosphates of zinc and calcium, oxides and hydroxides of calcium, zinc, barium, strontium and aluminium.

The powdered precursor may be comprised of a solid that will generate an acid in the presence of water or an acidic solution. Such a solid may be phosphorous pentoxide, disodium tartrate or disodium maleate.

The powdered precursor may also contain a peroxide initiator so that the powder-liquid mixture will undergo a free radical polymerisation in the absence of light. Suitable examples of such a peroxide initiator include: benzoyl peroxide or methyl ethyl ketone peroxide.

When preparing the glass ionomer cement, part, or all of the poly(carboxylic) acid component of the glass ionomer cement may be added to the powered precursor, also containing a spray-dried formulation in accordance with the present invention, so that the dry poly(carboxylic) acid polymer swells or dissolves in the liquid component, when the powdered and liquid precursors of the glass ionomer cement are mixed together.

Typically, the free radical polymerisation reaction is light activated and is brought about by adding to the liquid formulation, a small amount of an initiator such as camphorquinone and an activator such as a tetramethyl amine. A suitable example of such an amine is N,N-3,5-tetramethyl aniline. More typically, N,N-3,5-tetramethyl aniline may be present in a range of between 0.1% to 5% by weight based on the total of the liquid precursor of the glass ionomer cement. More typically, N,N-3,5-tetramethyl aniline is present in a range of between about 0.1 to about 0.7% by weight, and even more typically in a range between about 0.2 to about 0.5% by weight.

One method of obtaining the material of the pre-cured glass ionomer cement is via a free radical polymerisation reaction. The free radical polymerisation curing reaction is initiated by exposing the admixed liquid and powdered glass ionomer cement precursors to light that contains a significant amount of light at a wavelength at or close to 470 nm. The curing time may vary from about 5 to about 80 seconds, but more preferably from about 10 to about 60 seconds. An example of such a liquid source is provided by the Optilux 401 curing lamp (Demetron Research Corporation).

Alternative methods of obtaining the material of the pre-cured glass ionomer cement are to utilise a catonic or anionic polymerisation process. Combinations of Lewis acids and proton donors are important initiators for cationic polymerisation. A suitable combination includes boron trifluoride and water. Anionic polymerisation can be initiated by anionic species by transferring a negative change to the vinyl double bond, for example, potassium amide or a mixture of sodium and naphthalene.

The acid-base reaction that occurs to form a cured glass ionomer cement involves the neutralizing of the acid groups in the polymer network by multivalent metal ions such as calcium ions and aluminium ions as provided by the powdered precursor. The acid-base reaction is slow, and the rate of the reaction is limited by the diffusion of metal ions out of the glass powder into the polymer network, and subsequent ionic crosslinking.

The glass ionomer cement may also contain an amount of a heavy metal that would render the material opaque to X-rays, ie radio-opaque. Examples of such heavy metals include barium, bismuth, gold, silver, tin, lead, cadmium, antimony, palladium, platinum, tungsten or iridium. The heavy metals should be in a form sufficiently bound such that undesirable heavy metals are unable to be leached in vivo.

Generally, the glass ionomer cement exhibits fracture toughness and flexural modulus values similar to those obtained for classical glass ionomer cements, that is, about 0.4MNm and 6 GPa respectively after 72 hours of curing at ambient temperature.

Typically, the glass ionomer cement may be used as a dental restorative material.

Typically, the amount of formulation in accordance with the first embodiment of the invention, typically in a spray-dried form, present in the glass ionomer cement is between about 0.05 to about 50% of the cement. More typically, the amount of formulation is between about 0.05 and about 25%. Even more typically, the amount of formulation is between about 0.1 and about 20%.

Typically, the casein protein present in the formulation is a casein calcium phosphate complex.

According to a twenty-seventh embodiment of the invention, there is provided the formulation in accordance with the first embodiment of the invention, wherein the formulation additionally comprises a dispersing agent.

In general, the dispersing agent increases the rate that the phosphoprotein dissolves or disperses into solution or suspension, and in this way enhances the bioactivity. Typically, an aqueous solution or suspension of the formulation in accordance with the twenty-seventh embodiment of the invention can be sprayed onto foods such as breakfast cereal or flour, followed by drying. Alternatively, and more preferably, the formulation in accordance with the twenty-seventh embodiment of the invention is spray dried to form a powder. The spray dried powder can then be added to a beverages, a variety of foods, including confectionary, baked foods, and chewing gum etc, or for that matter may even be integrated into dental hygiene products, such as dental floss.

Typically, the dispersing agent present is selected from the group consisting of: sugars, carbohydrates, proteins, peptides, amino acids, lipids, urea, uric acid, and mixtures thereof.

Typically, a carbohydrate dispersing agent may be selected from the group consisting of: sugar, monosaccharides, disaccharides, oligosaccharides, polysaccharides and derivatives thereof.

Typically, a protein dispersing agent may be selected from the group consisting of: whey protein, glycoproteins, hydrolysed protein, and hydrolysed dephosphorylated protein.

Typically, a peptide dispersing agent may be selected from the group consisting of: adrenocorticotropic hormone and fragments, angiotensin and related peptides, atrial natriurertic peptides, bradykinin and related peptides, chemotactic peptides, dynorphin and related peptides endorphins and β-lipotropin fragments, enkephalin and related peptides, enzyme inhibitors, fibronectin fragments and related peptides, gastronintestinal peptides, growth hormone releasing peptides, luteinizing hormone releasing and related peptides, melanocyte stimulating hormone and related peptides, neurotensin and related peptides, opioid peptides oxytocin, vasopressin, vasotocin and related peptides, parathyroid hormone and fragments, protein kinase related peptides, somatostatin and related peptides, substance p and related peptides, and mixtures thereof.

Typically, an amino acid dispersing agent may be selected from the group consisting of: alanine, arginine, asparagine, aspartic acid, α-aminobuberic acid, cysteine, glutamine, glutamic acid, glycine, histidine, homoserine, hydroxyproline, isoleucine, leucine, lysine, methionine, norleucine, norvaline ornithine, pencillamine, prroglutamic acid, phenylalanine, proline, sarcosine, serine, staline, threonine, tyrptophan, tyrosine, valine and analogues and mixtures thereof.

Typically, the amount of casein protein, typically present as a phosphoprotein, present in the formulation in accordance with the twenty-seventh embodiment of the invention, is between 0.01 to 20%, more typically, between 0.1 to 10%, and even more typically, between 0.5 to 5%.

Typically, the amount of dispersing agent in the formulation in accordance with the twenty-seventh embodiment of the invention, is between 0.01 to 50%, more typically, between 0.1 to 20%, even more typically, between 0.5 to 5%.

The formulation in accordance with the twenty-seventh embodiment of the invention, typically, in a spray-dried form, can be incorporated in a form selected from the group consisting of: a toothpaste, mouthwash, food-stuff, beverage, pharmaceutical composition, dentifrice, lozenge, confectionary, or a glass ionomer cement. More typically, the food-stuff may include breakfast foods, such as cereals, and the confectionary may include chewing gum, candies, sweets, chocolates and other confectionary-like products.

Typically, the formulation in accordance with the twenty-seventh embodiment of the invention, typically, in a spray-dried form, can then be used in the formulations in accordance with any one of the second through to twenty-sixth embodiments of the invention.

According to a twenty-eighth embodiment of the invention, there is provided the formulation in accordance with the first embodiment of the invention, together with a salivary stimulator, wherein said formulation is capable of acting as a saliva substitute in humans or animals.

The saliva substitute may also further comprises any other type of bioactive ingredient that is typically found in the saliva of humans or animals.

Typically, said saliva substitute is used in patients with dysfunctional salivary ducts. More typically, said saliva substitute is transported from a reservoir to the back of the mouth.

Typically, the amount of casein protein, typically as a phosphoprotein, present the formulation in accordance with the twenty-eighth embodiment of the invention is between about 0.000001 to about 5%. More typically, the amount of casein phosphoprotein present in the formulation is between about 0.00001 to about 1%. Even more typically, the amount of casein phosphoprotein present in the formulation is between about 0.0001 to about 0.1%.

Typically, the saliva substitute to be provided to the patient is sterilised prior to use.

Typically, the salivary stimulator is pilocarpine.

Typically, the amount of salivary stimulator present in the saliva substitute in accordance with the twenty-eighth embodiment of the invention may range between about 0.00001% to about 10%; more typically, between about 0.001% to about 5%; still more typically, between about 0.01% to about 5%; yet still more typically, between about 0.01% to about 2%; even more typically, between about 0.1% to about 1%.

DEFINITIONS

The term "isolated and purified" means that the casein protein has been removed from milk, and associated impurities reduced or eliminated. In relation to this, it is known that casein in milk is present in a water insoluble, micellar form, and as a consequence, casein protein in accordance with the present invention has been isolated and purified therefrom. Essentially, it means an object species is the predominant species present (ie., on a molar basis it is more abundant than any other individual species in the composition), and preferably a substantially purified fraction is a composition wherein the object species comprises at least about 30 percent (on a molar basis) of all macromolecular species present. Generally, a substantially pure composition will comprise more than about 80 to 90 percent of all macromolecular species present in the composition. Most preferably, the object species is purified to essential homogeneity (contaminant species cannot be detected in the composition by conventional detection methods) wherein the composition consists essentially of a single macromolecular species.

By the phrase "suitable amount of a thickening agent" we mean that the formulation includes a sufficient amount of a thickening agent to form a thixotropic gel, but not so much of the thickening agent that the viscosity of the formulation is so great as to render the formulation unusable.

In the context of this specification, the term "comprising" means "including principally, but not necessarily solely".

Further, variations of the word "comprising", such as "comprise" and "comprises" have correspondingly varied meanings.

BEST MODES AND OTHER MODES OF CARRYING OUT THE INVENTION

In a typical form of the invention, a casein calcium phosphate complex is prepared by first dissolving in water a mixture of sodium caseinate (New Zealand Products, Australia Pty Ltd. 30 Frank St Wetherill Par,, NSW Australia) and disodium phosphate (Ajax Chemicals) (food grade), before adjusting the pH of the mixture to between about 8 to about 10. A solution of calcium chloride (2 mg/mL) (Ajax Chemicals) (food grade) is then added with agitation, and the mixture stirred until a homogeneous mixture is obtained. This homogeneous mixture provides a stock solution of the casein calcium phosphate complex comprising 100 mg/mL casein, 2 mg/mL calcium and 3.75 mg/mL phosphate.

Typically, in preparing the formulations of the present invention, the bioactive constituents, with the exception of calcium chloride and ethanol, are provided as solids, to be dissolved or maintained in aqueous solution or suspension.

Typically, a formulation of the present invention, wherein an inorganic bioactive constituent is associated with the casein protein, consists of the following and falls within the following ranges, wherein all proportions are expressed by weight:

| | |
|---|---|
| Casein calcium phosphate complex | 0.05 to 50% |
| Ethanol (absolute) | 0.05 to 15% |
| Water | up to 100% |

Typically, a further formulation of the present invention comprising inorganic bioactive constituents associated with the casein protein, falls within the following ranges, wherein all proportions are expressed by weight:

| | |
|---|---|
| Casein calcium phosphate complex | 0.05 to 3% |
| Ethanol (absolute) | 0.05 to 15% |
| Sodium fluoride | 5 ppm to 250 ppm |
| Water | up to 100% |

Typically, an even more preferred formation of the present invention, wherein the inorganic bioactive constituents are associated with the casein protein in the form of a thixotropic gel, falls within the following ranges, wherein all proportions are expressed by weight:

| | |
|---|---|
| Casein calcium phosphate complex | 0.1 to 3% |
| Ethanol (absolute) | 3 to 10% |
| Laponite | 0.1 to 10% |
| Titanium dioxide | 0.1 to 5% |
| Water | up to 100% |

Typically, a formulation of the present invention containing organic constituents associated with the casein protein, falls within the following ranges:

| | |
|---|---|
| Casein calcium phosphate complex | 0.5 to 25% |
| Sodium benzoate | 0.001 to 25% |
| Flavouring | Trace |
| Colouring | Trace |
| Water | up to 100% |

Typically, a formulation of the present invention containing organic constituents associated with the casein protein, falls within the following ranges:

| | |
|---|---|
| Casein calcium phosphate complex | 0.5 to 25% |
| Laponite | 0.5 to 12% |
| Ethanol (absolute) | 2 to 10% |
| Octyl methoxycinnamate | 0.1 to 0.8% |
| Water | up to 100% |

In general, the octyl methoxycinnamate is first dissolved in ethanol, and then added to remainder of the formulation with agitation.

Typically, a further formulation of the present invention, wherein the formulation contains organic constituents associated with the casein protein, falls within the following ranges:

| | |
|---|---|
| Casein calcium phosphate complex | 1 to 20% |
| Laponite | 0.5 to 12% |
| Ethanol (absolute) | 2 to 6% |
| Butyl methoxydibenzoylmethane | 0.1 to 0.8% |
| Water | up to 100% |

A still further formulation of the present invention, wherein the formulation contains organic constituents associated with the casein protein, falls within the following ranges:

| | |
|---|---|
| Casein calcium phosphate complex | 1 to 20% |
| Laponite | 0.5 to 12% |
| Ethanol (absolute) | 2 to 6% |
| Corticosteroid Hormone | 0.1 to 5% |
| Water | up to 100% |

A formulation of the present invention, wherein the formulation is useful in the treatment and/or prevention of dental caries and/or tooth erosion, falls within the following ranges:

| | |
|---|---|
| Casein calcium phosphate complex | 1 to 20% |
| Laponite | 0.5 to 12% |
| Ethanol (absolute) | 2 to 6% |
| Tetrasodium pyrophosphate | 0.01 to 25% |
| Water | up to 100% |

A further formulation of the present invention, wherein the formulation is useful in the treatment and/or prevention of dental sensitivity, falls within the following ranges:

| Casein protein | 1 to 20% |
| --- | --- |
| Laponite | 0.5 to 12% |
| Ethanol (absolute) | 2 to 6% |
| Strontium chloride | 0.01 to 20% |
| Water | up to 100% |

A still further formulation of the present invention, wherein the formulation is useful in the treatment and/or prevention of osteoporosis, falls within the following ranges:

| Casein calcium phosphate complex | 1 to 20% |
| --- | --- |
| Laponite | 0.5 to 12% |
| Ethanol (absolute) | 2 to 6% |
| Vitamin D | 0.1 to 100 mg/mL |
| Water | up to 100% |

A specific mouthwash formulation in accordance with present invention includes:

| Casein sodium phosphoprotein | 2.0% |
| --- | --- |
| Disodium phosphate | 0.115% |
| Calcium chloride dihydrate | 0.11% |
| Sodium benzoate | 0.03% |
| Sodium fluoride | 100 ppm |
| Flavour | 0.15% |
| Sodium saccharin | 0.08% |
| Ethanol (absolute) | 5.5% |
| Water | up to 100% |

Adjusted to pH 7.5 with 1N NaOH.

A specific thixotropic gel for use in a mouthguard in accordance with the present invention includes:

| Casein calcium phosphate complex | 1.0% |
| --- | --- |
| Disodium phosphate | 0.23% |
| Calcium chloride dihydrate | 0.22% |
| Sodium fluoride | 100 ppm |
| Sodium benzoate | 0.03% |
| Sodium saccharin | 1.6% |
| Flavour | 3.1% |
| Ethanol (absolute) | 5.5% |
| Water | up to 100% |
| Titanium dioxide | 1.0% |
| Laponite DF (synthetic clay) | 5% |

Adjusted to pH 7.5 with 1N NaOH.

A specific toothpaste in accordance with the present invention includes:

| Casein calcium phosphate complex | 2.5% |
| --- | --- |
| Disodium phosphate | 0.173% |
| Calcium chloride dihydrate | 0.165% |
| Sodium fluoride | 100 ppm % |
| Sodium benzoate | 0.03% |
| Sodium saccharin | 1.2% |
| Flavour | 2.3% |
| Ethanol (absolute) | 4.1% |
| Water | up to 100% |
| Titanium dioxide | 0.750% |
| Laponite DF | 5% |
| Silica abrasive | 20% |

Adjusted to pH 7.5 with 1N NaOH.

A formulation in accordance with the invention, additionally comprising a dispersant, includes:

| Casein calcium phosphate complex | 2.5% |
| --- | --- |
| Sugar | 2.5% |
| Disodium Phosphate | 0.12% |
| Calcium chloride, dihydrate | 0.12% |
| Ethanol (absolute) | 5.0% |
| Water | up to 100% |

Adjusted to pH 7.5 with 1N NaOH

A formulation of the present invention, wherein the formulation is subjected to spray-drying prior to incorporation in vehicle such as: chewing gums, lozenges, foods, beverages, confectionary, pharmaceutical compositions, toothpaste creams or gels, or mouthwashes, may be prepared as follows:

Firstly, a formulation comprising 10–20% sodium caseinate, 1–10% whey protein, to 1% disodium orthophosphate, and water up to 100% was mixed and stirred with an overhead stirrer until all the sodium caseinate is thoroughly dispersed.

Secondly, a formulation comprising 10–20% calcium chloride dihydrate (2 mg/mL) in water was prepared.

Thirdly, a formulation comprising approximately, 5% of the calcium chloride dihydrate solution and 95% of the caseinate solution was prepared.

Finally, a spray dried powder of the above formulation is obtained from a Niro Production Minor Spray Drier (Niro Australia Pty Ltd, Blackburn VIC, Australia), with an inlet temperature of about 200° C., and a flow rate that controlled the outlet temperature to about 85° C.

The resultant spray-dried powder formulation in accordance with the present invention is then added to vehicles such as: chewing gums, lozenges, foods, beverages, confectionary, pharmaceutical compositions, toothpaste creams or gels, or mouthwashes.

For example, a formulation of the present invention, in the form of a chewing gum may be prepared as follows:

A 2% by weight formulation in accordance with the first embodiment of the invention present in the form of a chewing gum comprising: 88% of a gum base, 2% of a spray-dried formulation in accordance with the first embodiment of the invention, wherein the spray-dried formulation comprises 4% calcium phosphate and 96% isolated and purified casein protein; 7% of a water-soluble bulking ingredient; 2% of a flavourant ingredient; and about 0.2% of a colourant; was prepared according to the following.

The gum base may comprise: elastomers, such as crown gum, in an amount of 25 to 55%, elastomer solvents, such as rosin esters, in an amount of 5–25%, waxes, such as paraffin, in an amount of 5–10%, and fillers, such as calcium carbonate in an amount of 15%.

The manner in which the gum base components are admixed is not critical and is performed using standard techniques and apparatus known to those skilled in the art and may be a traditional batch-type process or any extrusion-type process. In a typical method, an elastomer is admixed with an elastomer solvent and/or a plasticiser and/or an emulsifier and agitated for a period of time usually from 1 to 30 minutes. After blending is complete, the remaining ingredients may be added in bulk, incrementally, or stepwise while mixing until a homogeneous mass is obtained. The process may take from 15 minutes to 6 hours in a traditional batch type process. The final mass temperature may vary from 40° C. to 175° C. The final homogeneous mass is discharged from the mixer and allowed to cool and thereafter the gum base composition is incorporated into a chewing gum composition.

The amount of gum base employed in the chewing gum composition will vary depending on such factors as the type of product desired, the type of gum base used, the consistency desired, and the other components used to make the final chewing gum product.

Once prepared, the gum base together with the 2% by weight formulation in accordance with the first embodiment of the invention may be formulated to prepare a wide variety of chewing gum compositions, wherein the chewing gum compositions are prepared using standard techniques and equipment known to those skilled in the art. The apparatus useful in accordance with the present invention comprises mixing and heating apparatus well known in the chewing gum manufacturing arts, and therefore the selection of the specific apparatus would be readily apparent to the person skilled in the art.

In the administration of therapeutic formulations in accordance with any one of the second through to twenty-fifth embodiments of the present invention, there are preferred non-toxic pharmaceutical carriers, diluents, excipients and/or adjuvants. For administration, the formulations of the present invention are admixed with these non-toxic carriers, diluents, excipients and/or adjuvants and may be in the form of capsules, aqueous or oily suspensions, emulsions, syrups, pastes, elixirs, micelles or injectable solutions.

Examples of pharmaceutically acceptable carriers or diluents are demineralised or distilled water; saline solution; vegetable based oils such as peanut oil, safflower oil, olive oil, cottonseed oil, maize oil, sesame oils such as peanut oil, safflower oil, olive oil, cottonseed oil, maize oil, sesame oil, arachis oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane: cellulose derivatives such as methyl cellulose, ethyl cellulose, carboxymethylcellulose, sodium carboxymethylcellulose or hydroxypropylmethylcellulose; lower alkanols, for example ethanol or iso-propanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrridone; agar; carrageenan; gum tragacanth or gum acacia, and petroleum jelly. Typically, the carrier or carriers will form from 10% to 99.9% by weight of the compositions.

Some examples of suitable carriers, diluents, excipients and adjuvants for oral use include peanut oil, liquid paraffin, sodium carboxymethylcellulose, methylcellulose, sodium alginate, gum acacia, gum tragacanth, dextrose, sucrose, sorbitol, mannitol, gelatine and lecithin. In addition these oral formulations may contain suitable flavouring and colourings agents. When used in capsule form, such as in accordance with any one of the twentieth to twenty-second embodiments of the invention, the capsules may be coated with compounds such as glyceryl monostearate or glyceryl distearate which delay disintegration.

Adjuvants typically include emollients, emulsifiers, thickening agents, preservatives, bactericides, cytokines and buffering agents.

Solid forms for oral administration, such as in accordance with any one of the second to twenty-fifth embodiments of the invention, may contain binders acceptable in human and pharmaceutical practice, sweeteners, disintegrating agents, diluents, flavourings, coating agents, preservatives, lubricants and/or time delay agents. Suitable binders include gum acacia, gelatine, corn starch, gum tragacanth, sodium alginate, carboxymethylcellulose or polyethylene glycol. Suitable sweeteners include sucrose, lactose, glucose, aspartame or saccharine. Suitable disintegrating agents include corn starch, methylcellulose, polyvinylpyrrolidone, guar gum, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Liquid forms for oral administration may contain, in addition to the above agents, a liquid carrier. Suitable liquid carriers include water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides or mixtures thereof.

Suspensions for oral administration, such as in accordance with any one of the second to twenty-fifth embodiments of the invention may further comprise dispersing agents and/or suspending agents. Suitable suspending agents include sodium carboxymethylcellulose, methylcellulose, hydroxypropylmethyl-cellulose, poly-vinylpyrrolidone, sodium alginate or acetyl alcohol. Suitable dispersing agents include lecithin, polyoxyethylene esters of fatty acids such as stearic acid, polyoxyethylene sorbitol mono- or di-oleate, -stearate or -laurate, polyoxyethylene sorbitan mono- or di-oleate, -stearate or -laurate and the like.

The emulsions for oral administration may further comprise one or more emulsifying agents. Suitable emulsifying agents include dispersing agents as exemplified above or natural gums such as guar gum, gum acacia or gum tragacanth.

For administration as an injectable solution or suspension, non-toxic parenterally acceptable diluents or carriers can include: Ringer's solution, isotonic saline, phosphate buffered saline, ethanol and 1,2 propylene glycol.

It will be appreciated that the examples referred to above are illustrative only and other suitable carriers, diluents, excipients and adjuvants known to the art may be employed without departing from the spirit of the invention.

The formulations of the invention are typically formulated for administration by an oral or parenteral route, by inhalation or topical. The term parenteral as used herein includes intravenous, intradermal, intramuscular, subcutaneous, rectal, vaginal or intraperitoneal administration. However, oral forms of administration are generally preferred.

The oral dosage regimens for employing compounds of the invention to prophylactically or therapeutically treat osteoporosis in accordance with any one of the twentieth through to twenty-second embodiments of the invention, generally are in the range of about 1 to about 5000, preferably about 10 to about 1000, more preferably about 10 to about 500, even more preferably about 10 to about 1000, still more preferably about 10 to about 50, yet still more preferably about 10 to about 10, and yet even more preferably about 10 milligrams of formulation per kilogram body weight per day.

A pharmaceutical composition of the invention may also be administered by inhalation, that is, intranasal and/or oral inhalation administration. Appropriate dosage forms for such administration, such as an aerosol formulation or a metered dose inhaler, may be prepared by conventional techniques. The preferred dosage amount of a compound of the invention to be employed is generally within the range of about 0.05 to about 100, preferably about 0.05 to about 50, more preferably about 0.5 to about 25, even more preferably about 0.5 to about 10 milligrams per kilogram body weight per day.

A pharmaceutical composition of the invention may also be administered topically. By topical administration is meant non-systemic administration and includes the application of a pharmaceutical composition of the invention externally, for example, to the buccal cavity, where it does not significantly enter the blood stream. By systemic administration is meant oral, intravenous, intraperitoneal and intramuscular administration. The amount of the pharmaceutical composition of the invention required for therapeutic or prophylactic effect will, of course, vary with the pharmaceutical composition chosen, the nature and severity of the condition being treated and the animal undergoing treatment, and is ultimately at the discretion of the physician. A suitable topical dose of a pharmaceutical composition of the invention will generally be within the range of about 1 to about 100 milligrams per kilogram body weight daily, preferably about 0.05 to about 50, more preferably about 0.5 to about 25, even more preferably about 0.5 to about 10 milligrams per kilogram body weight per day.

Typically, a spray-dried formulation of the present invention may be incorporated into vehicles such as: chewing gums, lozenges, foods, beverages, confectionary, pharmaceutical compositions, toothpaste creams or gels, or mouthwashes, whereby the formulation of the present invention is administered at a rate of between 1 and 100 g per kg of dry weight of the vehicle, such as food. More typically, a spray-dried formulation of the present invention is administered at a rate of between 1 and 75 g per kg of dry weight of food. Even more typically, a spray-dried formulation of the present invention is administered at a rate of between 1 and 50 g per kg of dry weight of food. Yet even more typically, a spray-dried formulation of the present invention is administered at a rate of between 5 and 40 g per kg of dry weight of food. Yet still more typically, a spray-dried formulation of the present invention is administered at a rate of between 5 and 20 g per kg of dry weight of food.

The invention will now be described in greater detail by reference to specific Examples, which should not be construed as limiting on the scope thereof.

EXAMPLES

Example 1

A 5% by weight casein protein thixotropic gel formulation in accordance with the present invention was prepared according to the following:

The formulation involved adding 5% by weight of casein phosphoprotein sodium salt to 5% by weight ethanol, 0.06% sodium benzoate and 84.44% by weight water, and stirring with an overhead stirrer until the sodium caseinate has thoroughly dispersed.

Following this, about 5.5% by weight laponite was added, and the mixture stirred slowly for 24 hours with an overhead stirrer. When the stirrer was turned off the mixture formed a gel.

Example 2

A 2.5% by weight casein protein thixotropic gel formulation in accordance with the present invention was prepared according to the following:

1). Part A: adding 2.5% by weight of casein calcium phosphate complex and 0.24% by weight disodium phosphate to 5.26% by weight ethanol, 91.2% by weight water and 0.8% by weight 1N sodium hydroxide, and stirring with an overhead stirrer until the casein phosphoprotein is thoroughly dispersed.

2). Part B: dissolving 4.4% by weight calcium chloride di-hydrate (2 mg/mL) to 95.6% by weight water.

3). Adding 50 g Part B to 950 g of Part A, and stirring with an overhead stirrer until the system becomes homogeneous 4). Adding 55 g Laponite (or Laponite DF), and stirring with an overhead stirrer for 24 hr. When the stirrer was turned off, the mixture forms a stable gel.

Further, the formulation prepared in accordance with example 2 also provides a soluble source of both calcium and phosphate ions, useful in the remineralisation of teeth.

Example 3

A 10% by weight casein protein thixotropic gel formulation in accordance with the present invention was prepared according to the following:

Adding 10% by weight of casein phosphoprotein sodium salt and 0.03% by weight of sodium benzoate, to 5% by weight ethanol and 74.97% water. Stirring with an overhead stirrer until the sodium caseinate has thoroughly dispersed.

Then adding 10% by weight of Laponite and stirring with an overhead mixer for twenty-four hours. When the stirrer was turned off the mixture formed a gel.

Example 4

A thixotropic gel formulation in accordance with the present invention was prepared according to any one of Examples 1–3, wherein the formulation also included: 1% by weight of titanium dioxide.

Optionally, other metal containing compounds and inorganic compounds could also be added to form complexes with segments of the protein, or to be simply supported in the suspension by the gel structure provided by the clay.

Example 5

A thixotropic gel formulation in accordance with the present invention was prepared according to any one of Examples 1–3, wherein the formulation also included: 1% by weight of zinc oxide.

Optionally, other metal containing compounds and inorganic compounds could also be added to form complexes with segments of the protein, or to be simply supported in the suspension by the gel structure provided by the clay.

Example 6

A thixotropic gel formulation in accordance with the present invention was prepared according to any one of Examples 1–3, wherein the formulation also included: 1% by weight of zirconia.

Optionally, other metal containing compounds and inorganic compounds could also be added to form complexes with segments of the protein, or to be simply supported in the suspension by the gel structure provided by the clay.

Example 7

A thixotropic gel formulation in accordance with the present invention was prepared according to any one of Examples 1–3, wherein the formulation also included: 500 ppm of sodium fluoride.

Optionally, other metal containing compounds and inorganic compounds could also be added to form complexes with segments of the protein, or to be simply supported in the suspension by the gel structure provided by the clay.

Example 8

A thixotropic gel formulation, wherein the formulation also included: 0.2% by weight of a corticosteroid hormone was prepared according to the following:

The formulation was prepared by adding 5% by weight of casein phosphoprotein sodium salt to 86.3% by weight water, and stirring with an overhead stirrer until the sodium caseinate has thoroughly dispersed. 0.2% by weight cortisol was then dissolved in 5% by weight ethanol, and this solution was subsequently added to the aqueous protein solution whilst stirring with the overhead mixer.

Following this, 5.5% by weight of laponite was added, and the mixture stirred for twenty four hours. When the stirrer was turned off the mixture formed a gel.

Example 9

A thixotropic gel formulation, wherein the formulation also included: 0.8% by weight of a octyl methoxycinnamate, was prepared according to the following.

The formulation was prepared by adding 5% by weight of casein phosphoprotein sodium salt to 85.7% by weight water, and stirring with an overhead stirrer until the sodium caseinate has thoroughly dispersed. 0.8% by weight of a octyl methoxycinnamate was then dissolved in 5% by weight ethanol, and this solution was subsequently added to the aqueous protein solution whilst stirring with the overhead mixer.

Following this, 5.5% by weight of laponite was added, and the mixture stirred for twenty four hours. When the stirrer was turned off the mixture formed a gel.

Example 10

A thixotropic gel formulation in accordance with the invention was prepared according to any one of Examples 1–9, wherein the formulation also included: 0.1% by weight of flavourings.

Optionally, other metal containing compounds and inorganic compounds could also be added to form complexes with segments of the protein, or to be simply supported in the suspension by the gel structure provided by the clay.

Example 11

A thixotropic gel formulation in accordance with the invention was prepared according to any one of Examples 1–10, wherein the formulation also included: 0.1% by weight of colourings.

Optionally, other metal containing compounds and inorganic compounds could also be added to form complexes with segments of the protein, or to be simply supported in the suspension by the gel structure provided by the clay.

Example 12

A 2.5% casein protein formulation was prepared in the form of a gel, according to Example 2 above, and its stability was compared with the high viscosity formulation described in AU 604046.

In the formulation described in AU 604046, a precipitate was immediately observed to form. However, there was no evidence of a precipitate within the casein protein formulation of the present invention.

Similarly, a mouthwash was prepared according to Example 14 described below, and its stability compared with the mouthwash formulation outlined in AU 604046. Odorous bacterial breakdown was evident in the mouthwash formulation outlined in AU 604046 after two days. However, after a period of 12 months, there was no evidence of odorous bacterial breakdown within the mouthwash prepared in accordance with Example 14 of the present invention.

Example 13

A mouthwash in accordance with the present invention was prepared according to the following:

Adding 2% casein calcium phosphate complex and 0.1% peppermint flavour to 5% ethanol, 0.05% sodium benzoate and 92.85% water, and stirring with an overhead stirrer until the phosphoprotein was thoroughly dispersed.

Example 14

A mouthwash in accordance with the present invention was prepared according to the following:

1) Part A: Adding 3.0% casein phosphoprotein, 0.03% sodium benzoate, 0.1% sodium saccharin, and 0.13% disodium phosphate to 5.5% ethanol (absolute), 0.77% 1N sodium hydroxide, and 90.47% water, and stirring with an overhead stirrer until all the phosphoprotein was thoroughly dispersed.

2) Part B: Dissolving 2.2% calcium chloride di-hydrate (2 mg/mL) in 97.8% water.

3) Adding 50 g of Part B to 950 g of Part A, and stirring with an overhead mixer until a homogeneous mix was obtained.

Example 15

A formulation in accordance with the present invention for use in the treatment and/or prevention of dental caries and/or tooth erosion was prepared according to the following:

1). Part A: mixing 2.5% by weight of casein phosphoprotein, 5.26% by weight ethanol (absolute), 91.44% by weight water and 0.8% by weight 1N sodium hydroxide, and stirring with an overhead stirrer until the casein phosphoprotein is thoroughly dispersed.

2). Part B: dissolving 1.5% by weight tetrasodium pyrophosphate to 98.5% by weight water.

3). Adding 50 g Part B to 950 g of Part A, and stirring with an overhead stirrer until the system becomes homogeneous.

The formulation so prepared was then applied to the oral cavity of a subject, either as a dentifrice, in the form of a toothpaste, as a mouthwash, or after the addition of 10% by weight of laponite, as a thixotropic gel.

Example 16

A formulation in accordance with the present invention for use in the treatment and/or prevention of dental sensitivity was prepared according to the following:
1). Part A: mixing 2.5% by weight of casein phosphoprotein, 5.26% by weight ethanol (absolute), 91.44% by weight water and 0.8% by weight 1N sodium hydroxide, and stirring with an overhead stirrer until the casein phosphoprotein is thoroughly dispersed.
2). Part B: dissolving 1.2% by weight strontium chloride to 98.8% by weight water.
3). Adding 50 g Part B to 950 g of Part A, and stirring with an overhead stirrer until the system becomes homogeneous.

The formulation so prepared was then applied to the oral cavity of a subject, either as a dentifrice, in the form of a toothpaste, as a mouthwash, or after the addition of 10% by weight of laponite, as a thixotropic gel.

Example 17

A formulation in accordance with the present invention for use in the treatment and/or prevention of gingivitis was prepared according to the following:
1). Part A: Adding 0.3% casein phosphoprotein, 0.05% sodium benzoate, 0.1% sodium saccharin, and 0.13% disodium phosphate to 5.5% ethanol (absolute), 0.77% 1N sodium hydroxide, and 93.15% water, and stirring with an overhead stirrer until all the phosphoprotein was thoroughly dispersed.
2). Part B: Dissolving 2.2% calcium chloride di-hydrate (2 mg/mL) in 97.8% water.
3). Adding 50 g Part B to 950 g of Part A, and stirring with an overhead mixer until a homogeneous mix was obtained.

The formulation so prepared was then applied to the oral cavity of a subject, either as a dentifrice, in the form of a toothpaste, as a mouthwash, or after the addition of 10% by weight of laponite, as a thixotropic gel.

Example 18

A formulation in accordance with the present invention for use in treatment and/or prevention of mouth odour was prepared to the following:

Adding 2% casein calcium phosphate complex, 0.1% peppermint flavour and 0.05% sodium benzoate to 5.5% ethanol (absolute) and 92.35% water, and stirring with an overhead stirrer until the phosphoprotein was thoroughly dispersed.

The formulation so prepared was then applied to the oral cavity of a subject, either as a dentifrice, in the form of a toothpaste, as a mouthwash, or after the addition of 10% by weight of laponite, as a thixotropic gel.

Example 19

A thixotropic gel formulation in accordance with the present invention for use in the remineralisation of tooth structure was prepared according to the following:
1) Part A: Adding 2.5% casein phosphoprotein and 0.24% disodium phosphate to 5.26% ethanol (absolute), 91.2% water and 0.8% 1N sodium hydroxide, and stirring with an overhead stirrer until the phosphoprotein was thoroughly dispersed.
2) Part B: Dissolving 4.4% calcium chloride di-hydrate (2 mg/mL) to 95.6% water.
3) Adding 50 g Part B to 950 g of Part A, and stirring with an overhead stirrer until the system is homogeneous.
4) Adding 55 g Laponite (or Laponite DF) and 10 g of titanium dioxide, and stirring with an overhead stirrer for twenty-four hours. When the stirrer was turned off the mixture formed a gel.

The formulation so prepared was then applied to the oral cavity of a subject as a thixotropic gel.

Example 20

A formulation in accordance with the present invention for use in the modification of plaque to act as a buffer against a lowering of pH by bacteria was prepared according to the following:

Adding 2.5% calcium phosphate complex, 0.3% disodium phosphate and 0.1% peppermint flavour to 5% ethanol (absolute), 92.1% water, and stirring with an overhead stirrer until the phosphoprotein has thoroughly dispersed.

The formulation so prepared was then applied to the oral cavity of a subject, either as a dentifrice, in the form of a toothpaste, as a mouthwash, or after the addition of 10% by weight of laponite, as a thixotropic gel.

Example 21

A formulation in accordance with the present invention for use in the treatment and/or prevention of osteoporosis was prepared according to the following:
1) Part A: Adding 3.0% casein phosphoprotein, 0.1% sodium saccharin, and 0.13% disodium phosphate to 5.5% ethanol (absolute), 0.77% 1N sodium hydroxide, and 90.5% water, and stirring with an overhead stirrer until all the phosphoprotein was thoroughly dispersed.
2) Part B: Dissolving 2.2% calcium chloride di-hydrate (2 mg/mL) in 97.8% water.
3) Adding 50 g of Part B to 950 g of Part A, and stirring with an overhead mixer until a homogeneous mix was obtained.

The formulation so prepared was then orally administered to a subject

Example 22

A formulation in accordance with the present invention for use in the treatment and/or prevention of calculus was prepared according to the following:
1) Part A: Adding 2% w/w casein phosphoprotein sodium salt, 0.1% w/w sodium saccharin, and 1% tetrasodium pyrophosphate to 5.5% w/w ethanol (absolute), 0.7% w/w 1N sodium hydroxide, and 90.7% water, and stirring with an overhead stirrer until all the phosphoprotein was thoroughly dispersed.

The formulation so prepared was then applied to the oral cavity of a subject, either as a dentifrice, in the form of a toothpaste, as a mouthwash, or after the addition of 10% by weight of laponite, as a thixotropic gel.

Example 23

The formulation outlined in Example 14 above, or Example 24 below, may be spray-dried to form a powder, and then added to a glass ionomer cement.

Example 24

A formulation in accordance with the present invention, wherein the formulation is either sprayed on directly onto food stuff (wherein the food-stuff may be: confectionary, chewing gum or breakfast cereal), followed by drying, or firstly, spray dried to form a powder, which is then added to the food-stuff, wherein the formulation may be selected from the following:

| 1. | |
|---|---|
| Casein calcium phosphate complex | 5% |
| Water | 89.5% |
| Ethanol | 5% |
| Calcium chloride, dihydrate | 0.25% |
| Disodium hydrogen orthophosphate | 0.25% |
| 2. | |
| Casein calcium phosphate complex | 5% |
| Water | 89.4% |
| Ethanol | 5% |
| Calcium chloride, dihydrate | 0.25% |
| Disodium hydrogen orthophosphate | 0.25% |
| Vitamin D | 0.1% |
| 3. | |
| Casein calcium phosphate complex | 5% |
| Water | 89.4% |
| Ethanol | 5% |
| Calcium chloride, dihydrate | 0.25% |
| Disodium hydrogen orthophosphate | 0.25% |
| 4. | |
| Sodium caseinate | 10% |
| Water | 82.45% |
| Disodium orthophosphate | 0.75% |
| 4N Sodium hydroxide | 1.0% |
| Hydrolysed whey protein | 5% |
| Calcium chloride, dihydrate | 0.8% |

These mixtures could also be added to a beverage, or used as a liquid medicine, and may also include other proteins and amino acids that will provide nutritional value. Also, these could also be used to generate tablets by spray drying the formulation so prepared, followed by pressing into tablet form.

Also, the formulation of the present invention can be encapsulated or microencapsulated with waxes, fats, starch, hydrogenated vegetable oils, proteins, maltodextrose, mono- or di-glycerides, polyvinylpyrrolidone, polyethylene, nylon, gum arabic, gelatin and cellulose-based compounds. Encapsulation can be achieved by spray drying, coacervation phase separation, multiorifice-centrifugal extrusion, air suspension coating or pan coating.

Example 25

A formulation in accordance with the present invention, to be sprayed on food, such as breakfast cereal, was prepared according to the following:
1) Part A: Adding 2.5% casein phosphoprotein, 2.0% sugar, 5.5% ethanol, 0.13% disodium phosphate, 89.07% water, and 0.8% 1N sodium hydroxide, and stirring with an overhead stirrer until all the phosphoprotein has thoroughly dispersed.
2) Part B: Dissolving 2.2% calcium chloride, dihydrate in 97.8% water.
3) Adding 50 g of Part B to 950 g of Part A, at the same time stirring. Stir with an overhead mixer until a homogeneous mix is obtained.

Example 26

A formulation in accordance with the present invention, subsequently spray dried, for addition to food products, such as confectionary, was prepared according to the following:

1) Part A: Adding 16% sodium caseinate, 5% whey protein, 0.75% disodium orthophosphate, 77.25% water, and stirring with an overhead stirrer until all the sodium caseinate is thoroughly dispersed.
2) Part B: Dissolving 16% calcium chloride dihydrate in 84% water.
3) Adding 50 g of Part B to 950 g of Part A, and stirring with an overhead mixer until a homogenous mix was obtained.

Finally, a spray dried powder of the above formulation is obtained from a Niro Production Minor Spray Drier (Niro Australia Pty Ltd. Blackburn, VIC, Australia), with an inlet temperature of about 200° C., and a flow rate that controlled the outlet temperature to about 85° C.

Example 27

A light curable glass ionomer cement was prepared according to the following:

| (a) Liquid Precursor:— | |
|---|---|
| Poly(acrylic acid) | 26.0 grams |
| Methacrylic acid | 16.0 grams |
| 1,5-diallyl-2,4-benzene dicarboxylic acid | 8.0 grams |
| Water | 50 ml |
| N,N-3,5-tetramethyl aniline | 0.36 grams |
| Camphorquinone | 0.34 grams |
| Butylated hydroxytoluene | 0.20 grams |
| (b) Powder Precursor:— | |
| Calcium aluminium fluorosilicate glass powder | 99.8% |
| Benzoyl peroxide | 0.2% |
| Casein phosphoprotein sodium salt (spray-dried) | 5% |

The powder:liquid ratio is 1.5:1.

The powdered and liquid precursors of the glass ionomer cement, together with the formulation of the present invention are supplied separately. A paste is produced in small quantities as required by introducing small amounts of the liquid precursor, to the powdered precursor on a suitably sized plate or mixing receptacle. The liquid and powder precursors are then mixed.

The resulting composition is then cured to an elastomeric state by a free radical polymerisation process. This process is preferably catalysed by light curing. The composition is mixed with an appropriate photoinitiator, either UV or visible light sensitive and an amine accelerator. A free radical inhibitor is added to improve the shelf life of the liquid precursor. An acid-base reaction occurs between the acid groups of the polymer network and the divalent and trivalent metal ions of the powdered precursor to produce a glass ionomer cement.

Example 28

A light curable glass ionomer cement was prepared according to the following:

| (a) Liquid Precursor:— | |
|---|---|
| Poly(acrylic acid) | 18.0 grams |
| Methacrylic acid | 16.0 grams |
| 1,5-diallyl-2,4-benzene dicarboxylic acid | 16.0 grams |
| Water | 50 ml |
| N,N-3,5-tetramethyl aniline | 0.36 grams |

-continued

| | |
|---|---|
| Camphorquinone | 0.34 grams |
| Butylated hydroxytoluene | 0.02 grams |
| (b) Powder Precursor:— | |
| Calcium aluminium fluorosilicate glass powder | 99.8% |
| Benzoyl peroxide | 0.2% |
| Casein phosphoprotein sodium salt (spray-dried) | 5% |

The powder:liquid ratio is 1.5:1.

The glass ionomer cement is produced in accordance with the method described in Example 27.

Example 29

A novel light curable glass ionomer cement was prepared according to the following:

| | |
|---|---|
| (a) Liquid Precursor:— | |
| Poly(acrylic acid) | 18.0 grams |
| Methacrylic acid | 20.0 grams |
| 1,5-diallyl-2,4-benzene dicarboxylic acid | 12.0 grams |
| Water | 50 ml |
| N,N-3,5-tetramethyl aniline | 0.36 grams |
| Camphorquinone | 0.34 grams |
| Butylated hydroxytoluene | 0.02 grams |
| (b) Powder Precursor:— | |
| Calcium aluminium fluorosilicate glass powder | 79.8% |
| Barium glass | 20.0% |
| Benzoyl peroxide | 0.2% |
| Casein phosphoprotein sodium salt (spray-dried) | 5% |

The glass ionomer cement is produced in accordance with the method described in Example 27.

Example 30

A formulation for use as a saliva substitute in the oral cavity of humans or animals was prepared according to the following:
1) Part A: Adding 3.0% phosphoprotein, 0.13% disodium phosphate, 0.77% 1N sodium hydroxide, and 96.1% water, and stirring with an overhead stirrer until all the phosphoprotein was thoroughly dispersed.
2) Part B: Dissolving 2.2% calcium chloride dihydrate in 97.8% water.
3) Adding 50 g of Part B to 950 g of Part A, and stirring with an overhead mixer until a homogenous mix was obtained.
4) Diluting stock solution by adding 100 liters of water.

Example 31

A formulation for use as a saliva substitute in the oral cavity of humans or animals was prepared according to Example 30, wherein the additional materials, pilocarpine (1% w/w), ethanol (5%) and optionally, peppermint flavouring (0.1%).

When preparing the formulations of the present invention as exemplified above, the constituents, with the exception of calcium chloride and ethanol, are provided as solids, subsequently, dissolved or maintained in aqueous solution or suspension.

INDUSTRIAL APPLICABILITY

The formulation of the present invention can be used to deliver bioactive constituents to biological surfaces, in particular, but not limited to, dental surfaces.

What is claimed is:

1. A confectionary formulation for the delivery of bioactive constituents to biological surfaces, wherein said formulation comprises an aqueous or dried solid confectionary base, a water soluble form of at least one isolated and purified casein phosphoprotein, or salt thereof, complexed with at least one bioactive constituent, wherein the bioactive constituent is selected from the group consisting of calcium phosphate and calcium phosphate admixed with at least one other bioactive.

2. The formulation of claim 1, wherein said casein protein is selected from the group consisting of: α-casein, β-casein, κ-casein, and mixtures thereof.

3. The formulation of claim 1, wherein said casein phosphoprotein is in the form of caseinate calcium phosphate or caseinate calcium fluorophosphate.

4. The formulation of claim 3, wherein the amount of casein calcium phosphate present in the formulation is between about 0.05 and 50% by weight.

5. The formulation of claim 1, wherein said bioactive constituents comprise ions selected from the group consisting of: calcium, phosphate, fluorophosphates, fluoride, magnesium, barium, strontium, zinc, iron, copper, aluminium, tin; and salts of said bioactive constituents selected from the group consisting of: titanium dioxide, zinc oxide, zirconia, calcium fluoride, sodium fluoride, stannous fluoride, sodium monofluorophosphate, zinc ammonium fluoride, tin ammonium fluoride, cobalt ammonium fluoride calcium phosphate, calcium fluorophosphates and calcium oxide.

6. The formulation of claim 1, wherein said bioactive constituent is an antimicrobial agent.

7. The formulation of claim 6, wherein the anti-microbial agent is selected from the group consisting of: halogenated diphenyl esters, phenolic compounds, mono- and poly-alkyl and aromatic halophenols, resorcinol, n-methyl hexyl resorcinol; bisphenolic compounds and halogenated carbanilides.

8. The formulation of claim 6, wherein the anti-microbial agent is selected from the group consisting of: glycerol, ethanol sorbitol, mannitol, sodium benzoate, methyl-p-hydroxybenzoate, ethyl-p-hydroxybenzoate, N-propyl p-hydroxybenzoate, butyl-p-hydroxybenzoate, phenoxy ethanol, benzethonium chloride, and diisobutyl-phenoxyethoxyethyl dimethyl benzyl ammonium chloride.

9. The formulation of claim 8, wherein said antimicrobial agent is sodium benzoate or ethanol.

10. The formulation of claim 9, wherein the amount of sodium benzoate present in the formulation is between 0.001 and 0.1% by weight.

11. The formulation of claim 10, wherein the amount of ethanol present in the formulation is between about 2 and 6% by weight.

12. The formulation of claim 1, wherein said formulations also includes a thickening agent.

13. The formulation of claim 12, wherein said thickening agent is selected from the group consisting of: clay, polymer, or a combination thereof.

14. The formulation of claim 13, wherein said clay is selected from the group consisting of laponite, laponite DF, hectorite, calcium montmorillonite, sodium montmorillonite (bentonite), sodium exchanged montmorillonite, acid activated bleaching earth and palygorskite.

15. The formulation of claim 13, wherein said polymer is selected from the group consisting of: alginate, cellulose, carboxymethyl cellulose, Irish moss, gum tragacanth, starch polyvinylpyrrolidone, hydroxyethylpropylcellulose, hydroxybutyl methyl cellulose, hydroxypropyl methyl cellulose, hydroxyethyl cellulose, sodium carboxymethyl cellulose, and colloidal silica.

16. The formulation of claim 12, wherein the amount of thickening agent present in the formulation is up to about 20% by weight.

17. A method for treating and/or preventing dental caries and/or tooth erosion in humans or animals in need of said treatment and/or prevention, said method comprising administering a therapeutically effective amount of the formulation of claim 1, wherein said formulation is capable of controlling or preventing dental caries and/or tooth erosion in humans or animals.

18. The method of claim 17, wherein said bioactive constituents of the formulation are selected from the group consisting of: tetrasodium pyrophosphate; N-methylpyrrolidone or 2-pyrrolidone-5,5-diethyl phosphonic acid.

19. A method of treating and/or preventing dental sensitivity in humans or animals in need of said treatment and/or prevention, said method comprising administering a therapeutically effective amount of the formulation of claim 1, wherein said formulation is capable of controlling and/or preventing dental sensitivity in humans or animals.

20. The method of claim 19, wherein said bioactive constituents are selected from the group consisting of: glycerine, strontium chloride, sodium citrate, potassium nitrate and dicalcium phosphate.

21. A method of treating and/or preventing gingivitis in humans or animals in need of said treatment and/or prevention, said method comprising administering a therapeutically effective amount of the formulation of claim 1, wherein said formulation is capable of controlling and/or preventing gingivitis in humans or animals.

22. A method of treating or preventing mouth odour in humans or animals in need of said treatment and/or prevention, said method comprising administering a therapeutically effective amount of the formulation of claim 1, wherein said formulation is capable of controlling or preventing mouth odour in humans or animals.

23. The method of claim 21, wherein said bioactive constituent include an antimicrobial agent.

24. The method of claim 23, wherein said anti-microbial agent is selected from the group consisting of halogenated diphenyl ethers, phenolic compounds, mono- and poly-alkyl and aromatic halophenols, resorcinol, n-methyl hexyl resorcinol, bisphenolic compounds, and halogenated carbanilides.

25. A method of recrystallising and/or remineralising enarnel and/or dentine in humans or animals in need of said recrystallising and/or remineralising, said method comprising administering an effective amount of the formulation of claim 1, wherein said formulation is capable of recrystallising and remineralising enamel and/or dentine in humans or animals.

26. The method of claim 26, wherein said the bioactive constituents are selected from the group consisting of: fluoride, a calcium phosphate complex and a calcium fluorophosphate complex.

27. A method of buffering plaque against a decrease in pH in humans or animals in need of said buffering, said method comprising administering an effective amount of the formulation of claim 1, wherein said formulation is capable of buffering plaque against a fall in pH in humans or animals.

28. A method of treating and/or preventing osteoporosis in humans or animals in need of said treatment and/or prevention, said method comprising administering a therapeutically effective amount of the formulation of claim 1, wherein said formulation is capable of controlling or preventing osteoporosis in humans or animals.

29. The method of claim 28, wherein said bioactive constituents are selected from the group consisting of: vitamin D, calcium phosphate complex and/or calcium fluorophosphate complex, wherein said calcium phosphate complex and/or calcium fluorophosphate complex provides a soluble (bioavailable) source of calcium.

30. A method of treating and/or preventing calculus formation in the oral cavity of humans or animals in need of said treatment and/or prevention, comprising administering a therapeutically effective amount of the formulation of claim 1, wherein said formulation is capable of controlling and/or preventing calculus formation in the oral cavity of humans or animals.

31. The method of claim 30, wherein said bioactive constituents are selected from the group consisting of: casein phosphoprotein, tetrasodium pyrophosphate, tetrapotassium pyrophosphate, and mixtures thereof.

32. The formulation of claim 1, wherein said formulation additionally comprises a dispersing agent.

33. The formulation of claim 32, wherein said dispersing agent is selected from the group consisting of: sugars, carbohydrates, proteins, peptides, amino acids, lipids, urea, uric acid, and mixtures thereof.

34. The formulation of claim 33, wherein said carbohydrate is selected from the group consisting of: sugar, monosaccharides, disaccharides, oligosaccharides, polysaccharides and derivatives thereof.

35. The formulation of claim 33, wherein said protein is selected from the group consisting of: whey protein, glycoproteins, hydrolysed proteins and hydrolysed dephosphorylated proteins.

36. The formulation of claim 33, wherein said peptide is selected from the group consisting of: adrenocorticotropic hormone and fragments, angiotensin, atrial natriurertic peptides, bradykinin, chemotactic peptides, dynorphin, endorphins and β-lipotropin fragments, enkephalin, enzyme inhibitors, fibronectin fragments, gastrointestinal peptides, growth hormone releasing peptides, luteinizing hormone releasing peptides, melanocyte stimulating hormone, neurotensin, opioid peptides, oxytocin, vasopressin, vasotocin, parathyroid hormone and fragments, protein kinase related peptides, somatostatin, substance p, and mixtures thereof.

37. The formulation of claim 33, wherein said amino acid is selected from the group consisting of: alanine, arginine, asparagine, aspartic acid, α-aminobuberic acid, cysteine, glutamine, glutamic acid, glycine, histidine, homoserine, hydroxyproline, isoleucine, leucine, lysine, methionine, norleucine, norvalineornithine, pencillamine, proglutamic acid, phenylalanine, proline, sarcosine, serine, staline, threonine, tyrptophan, tyrosine, valine and analogues and mixtures thereof.

38. The formulation of claim 1, further comprising a salivary stimulator, wherein said formulation acts as a salivary substitute in humans or animals.

39. The formulation of claim 38, wherein said salivary stimulator is pilocarpine.

40. The formulation of claim 1, wherein said formulation is pre-dried prior to use in solid form.

41. The formulation of claim 1, wherein said formulation is pre-dried prior to resuspension in aqueous form.

42. The formulation of claim 7, wherein halogenated diphenyl ether is 2',4,4'-trichloro-2-hydroxy-diphenyl ether (Triclosan).

43. The formulation of claim 7, wherein said phenolic compound is selected from the group consisting of 2-methyl-phenol, 3-methyl-phenol, 4-methyl-phenol, 4-ethyl-phenol, 2,4-dimethylphenol, 3,4-dimethyl-phenol, 2,6-dimethyl-phenol, and 2,2-methylene bis (4-chloro-6-bromophenol).

44. The formulation of claim 7, wherein said mono- and poly-alkyl and aromatic halophenol is selected from the group consisting of methyl-p-chlorophenol, ethyl-p-chlorophenol, n-propyl-p-chlorophenol, n-butyl-chlorophenol, o-chlorophenols, p-bromophenols and -o-bromophenols.

45. The method of claim 24, wherein said halogenated diphenyl ether is 2',4,4'-trichloro-2-hydroxydiphenyl ether (Triclosan).

46. The method of claim 24, wherein said phenolic compound is selected from the group consisting of 2-methyl-phenol, 3-methyl-phenol, 4-methyl-phenol, 4-ethyl-phenol, 2,4-dimethylphenol, 3,4-dimethyl-phenol, 2,6-dimethyl-phenol, and 2,2-methylene bis (4-chloro-6-bromo-phenol).

47. The method of claim 24, wherein said mono- and poly-alkyl and aromatic halo-phenol is selected from the group consisting of methyl-p-chlorophenol, ethyl-p-chlorophenol, n-propyl-p-chlorophenol, n-butyl chlorophenol; -o-chlorophenols; p-bromophenols; and -o-bromophenols.

48. The formulation of claim 1, wherein said confectionary formulation is a chewing gum.

* * * * *